US012270023B2

(12) United States Patent
Cuero Rengifo et al.

(10) Patent No.: US 12,270,023 B2
(45) Date of Patent: Apr. 8, 2025

(54) CARBO-IONIC CULTURES AND EXTRACTS AND APPLICATIONS THEREOF

(71) Applicant: Bio Capital Holdings, LLC, Houston, TX (US)

(72) Inventors: Raul Cuero Rengifo, Cypress, TX (US); Juliana Londoño Murillo, Manizales (CO); Isabela Giraldo Badillo, Aranzazu (CO); Tatiana Varela Toro, Manizales (CO); Johny Mateo Sanchez Giraldo, Manizales (CO); María Díaz Sánchez, Bogotá (CO)

(73) Assignee: Bio Capital Holdings, LLC, Houston, TX (US)

(*) Notice: Subject to any disclaimer, the term of this patent is extended or adjusted under 35 U.S.C. 154(b) by 778 days.

(21) Appl. No.: 17/438,160

(22) PCT Filed: Mar. 10, 2020

(86) PCT No.: PCT/US2020/021881

§ 371 (c)(1),
(2) Date: Sep. 10, 2021

(87) PCT Pub. No.: WO2020/185773

PCT Pub. Date: Sep. 17, 2020

(65) Prior Publication Data

US 2022/0145240 A1 May 12, 2022

Related U.S. Application Data

(60) Provisional application No. 62/817,710, filed on Mar. 13, 2019.

(51) Int. Cl.

| | |
|---|---|
| ***A61K 8/99*** | (2017.01) |
| ***A01N 63/20*** | (2020.01) |
| ***A61K 35/74*** | (2015.01) |
| ***A61Q 17/04*** | (2006.01) |
| ***C12N 1/18*** | (2006.01) |
| ***C12N 1/20*** | (2006.01) |
| *H01M 10/36* | (2010.01) |

(52) U.S. Cl.
CPC ............... *C12N 1/20* (2013.01); *A01N 63/20* (2020.01); *A61K 8/99* (2013.01); *A61K 35/74* (2013.01); *A61Q 17/04* (2013.01); *C12N 1/18* (2013.01); *H01M 10/36* (2013.01); *H01M 2300/0002* (2013.01)

(58) Field of Classification Search
CPC ........................................................ A61K 8/99
See application file for complete search history.

(56) References Cited

U.S. PATENT DOCUMENTS

2016/0023933 A1* 1/2016 Wong ...................... C02F 3/341 435/252.4

FOREIGN PATENT DOCUMENTS

| | | | |
|---|---|---|---|
| CN | 104830740 A | * | 8/2015 |
| CN | 105576302 | | 2/2018 |
| JP | 60239495 A | * | 11/1985 |
| WO | 20180213526 | | 11/2018 |

OTHER PUBLICATIONS

International Search Report and Written Opinion for Application No. PCT/US2020/021881 mailed May 28, 2020.

* cited by examiner

*Primary Examiner* — Qiuwen Mi
(74) *Attorney, Agent, or Firm* — Thomas|Horstemeyer, LLP

(57) ABSTRACT

Described herein are carbo-ionic cultures and extracts and applications thereof. The carbo-ionic cultures are grown in media containing an organic component and an inorganic component and the proportions and compositions of these components can be tailored to produce carbo-ionic extracts with specific properties such as, for example, the ability to provide power to a light emitting diode (LED) with a specific voltage. The carbo-ionic cultures and extracts have further uses including enhancing the growth of plants, including plants grown from tissue culture, and as supplemental nutrients for cultures of industrially, commercially, and/or scientifically-important microorganisms. Also described herein are microbial electric circuits comprising the carbo-ionic cultures and extracts described herein as well as applications of those circuits.

22 Claims, 8 Drawing Sheets

CARBO-IONIC CULTURES AND EXTRACTS AND APPLICATIONS THEREOF

CROSS REFERENCE TO RELATED APPLICATIONS

This application claims priority upon U.S. provisional application Ser. No. 62/817,710 filed on Mar. 13, 2019. This application is hereby incorporated by reference in its entirety.

BACKGROUND

Battery-powered devices are useful in applications ranging from telecommunications to medical devices to providing light during power outages. Current battery technology has several drawbacks, however. Although alkaline batteries can be recycled, few facilities exist for doing so and many end up in landfills each year. Alkaline batteries are also prone to leakage as they age and are used, which can ruin electronic devices. Lead-acid batteries are bulky, contain toxic metals, and may overheat during charging; they may also leak electrolytes (including corrosive acids) under improper storage conditions. Lithium-ion batteries are typically small and rechargeable, but charge cycles are limited and transportation restrictions exist due to the possibility of short circuits leading to fires.

It would be advantageous to develop a new, inexpensive, portable power source that is effective and poses no environmental hazards during the disposal process. It would further be advantageous if this power source could make use of water-based electrolyte solutions and did not present a fire hazard during transportation or storage. It would further be advantageous if the raw materials used to generate the electrolyte solutions, or the electrolyte solutions themselves had other applications in agriculture, including plant tissue culture applications; commercial microorganism culture, including growth of organisms that produce industrially important compounds such as ethanol, acetic acid, rennet, insulin, and related compounds; and the like, either as a separate use or as a use for electrolyte solutions that have aged out of useful life. The present invention addresses these needs.

SUMMARY

Described herein are carbo-ionic cultures and extracts and applications thereof. The carbo-ionic cultures are grown in media containing an organic component and an inorganic component and the proportions and compositions of these components can be tailored to produce carbo-ionic extracts with specific properties such as, for example, the ability to provide power to a light emitting diode (LED) with a specific voltage. The carbo-ionic cultures and extracts have further uses including enhancing the growth of plants, including plants grown from tissue culture, and as supplemental nutrients for cultures of industrially, commercially, and/or scientifically-important microorganisms. Also described herein are microbial electric circuits comprising the carbo-ionic cultures and extracts described herein as well as applications of those circuits.

The advantages of the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
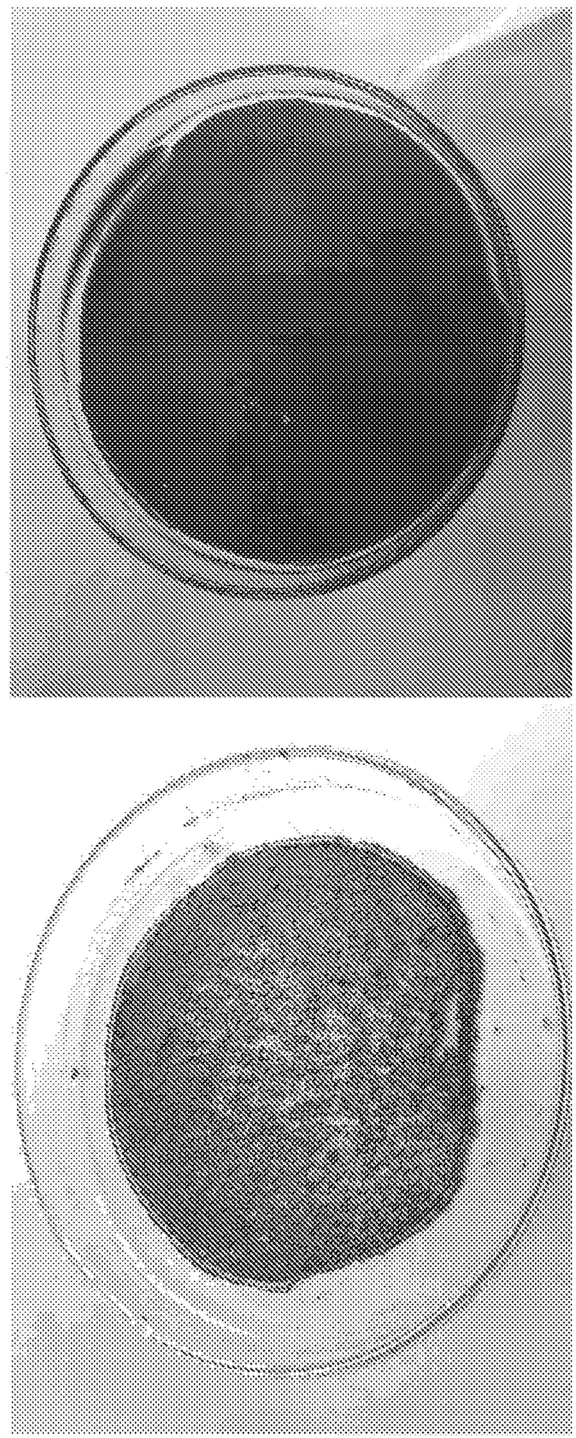
FIG. 1 shows *Acidithiobacillus ferrooxidans* grown in a culture medium consisting of 50% organic content and 50% inorganic content (50/50 medium described herein). Colonies are approximately 50% black and 50% brown.

Before the present compounds, compositions, articles, devices, and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "a potassium salt" includes mixtures of two or more such potassium salts, and the like.

"Optional" or "optionally" means that the subsequently described event or circumstance can or cannot occur, and that the description includes instances where the event or circumstance occurs and instances where it does not. For example, the phrase "optionally includes a cobalt salt" means that the cobalt salt may or may not be present.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint and independently of the other endpoint.

"Admixing" or "admixture" refers to a combination of two or more components together wherein there is no chemical reaction or physical interaction. The terms "admixing" and "admixture" can also include the chemical reaction or physical interaction between any of the components described herein upon mixing to produce the composition. The components can be admixed alone, in water, in another solvent, or in a combination of solvents.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed that while specific reference to each various individual and collective combination and permutation of these compounds may not be explicitly disclosed, each is specifically contemplated and described herein. For example, if a bacterium is disclosed and discussed and a number of different iron salts are discussed, each and every combination and permutation of bacterium and iron salt that is possible is specifically contemplated unless specifically indicated to the contrary. For example, if a class of molecules A, B, and C are disclosed as well as a class of molecules D, E, and F, and an example of a combination molecule, A-D, is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the subgroup of A-E, B-F, and C-E is specifically contemplated and should be considered disclosed from disclosure of A, B, and C; D, E, and, F; and the example combination A-D. This concept applies to all aspects of this disclosure including, but not limited to, steps in methods of making and using the disclosed compositions. Thus, if there are a variety of additional steps that can be performed, it is understood that each of these additional steps can be performed with any specific embodiment or combination of embodiments of the disclosed methods, and that each such combination is specifically contemplated and should be considered disclosed.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5 and are present in such ratio regardless of whether additional components are contained in the compound.

A weight percent of a component, unless specifically stated to the contrary, is based on the total weight of the formulation or composition in which the component is included.

Described herein are carbo-ionic cultures and extracts capable and their applications thereof. The cultures are grown in media containing an organic component and an inorganic component and the proportions and compositions of these components can be tailored to produce extracts with specific properties such as, for example, the ability to provide power to a light emitting diode (LED) with a specific voltage. The cultures and extracts have further uses including enhancing the growth of plants, including plants grown from tissue culture, and as supplemental nutrients for cultures of industrially, commercially, and/or scientifically-important microorganisms. Also described herein are microbial electric circuits comprising the microbial cultures and extracts described herein as well as applications of those circuits.

I. Microorganisms

Various microorganisms are contemplated for use in producing the compositions, extracts, and devices disclosed herein. In one aspect, the microorganisms have metabolisms that require or are facilitated by free iron. In another aspect, they can be iron-oxidizing bacteria, siderophilic bacteria, dissimilatory metal-reducing microorganisms, halophilic sulfur-oxidizing bacteria, algae, thermophilic bacteria and/or archaea, chemoautotrophic bacteria, chemolithotrophic bacteria, actinomycetes, other fungi, or similar microorganisms.

In some aspects, one or both of the following processes are active in cultures of the microorganisms contemplated herein, or can be made active depending on culture conditions including pH, temperature, nutrient sources, oxygen concentration, and the like:

$$4H_2O+2Fe_2O_3 \rightarrow 4Fe(OH)_2+O_2$$

$$4Fe(OH)_2+O_2 \rightarrow 4H_2O+2Fe_2O_3$$

In one aspect, the microorganisms can be *Acidithiobacillus ferroxidans, Thiobacillus ferroxidans, Leptospirillum ferroxidans, Vibrio vulnificus, Listeria monocytogenes, Yersinia enterocolica, Salmonella enterica, Klebsiella pneu-*

*monia, Escherichia coli, Rhizopus arrhizus*, or a *Mucor* species. In another aspect, the microorganisms can be a *Thermoanaerobacter* species such as, for example, *T. acetoethylicus, T. brockii, T. ethanolicus, T. italicus, T. kivui, T. mathranii, T. pseudoethanolicus, T. siderophilus, T. sulfurigignens, T. sulfurophilus, T. thermocopriae, T. thermohydrosulfuricus, T. thermosaccharolyticum, T. uzoensis*, or *T. wiegelii*. In another aspect, the microorganisms can be selected from *Albidiferax ferrireducens, Shewanella oneidensis, Shewanella haliotis, Geobacter metallireducens, G. uraniireducens, G. sulfurreducens, Geothrix fermentans, Deferribacter abyssi, Deferribacter autotrophicus, Deferribacter desulfuricans, Deferribacter thermophilus*, or a similar species.

In another aspect, the microorganisms can be halophilic sulfur-oxidizing bacteria such as, for example, *Acidithiobacillus thiooxidans, Acidithiobacillus caldus, Nitrosococcus oceani, Allochromatium vinosum, Halorhodospira halophile, Nitrococcus mobilis, Alkalispirillum mobilis, Thiobacillus prosperus, Thioalkalispira microaerophila, Ectothiorhodospira haloalkalophila, Thioalkalivibrio versutus, Halothiobacillus kellyi, Halothiobacillus neapolitanus, Halothiobacillus ILL* 27, *Halothiobacillus halophilus, Halothiobacillus HL* 1, *Halothiobacillus hydrothermalis, Halothiobacillus HL-U*1, *Dechloromarinus chlorophilus, Lucina pectinata, Thioalkalimicrobium aerophilum, Thiomicrospira pelophila, Thiomicrospira HL* 5, *Thiomicrospira kuenenii, Thiomicrospira crunogena, Halomonas halophile*, or a similar species.

In yet another aspect, the microorganisms can be algae and/or diatoms such as, for example, *Skeletonema costatum, Alexandrium catenella, Phaeodactylum triornutum*, or a similar species. In one aspect, the algae and/or diatoms can be a *Pseudo-nitzschia* species such as, for example, *P. abrensis, P. americana, P. antarctica, P. arctica, P. arenysensis, P. australis, P. batesiana, P. bipertita, P. brasiliana, P. bucculenta, P. caciantha, P. calliantha, P. circumpora, P. cuspidate, P. decipiens, P. delicatissima, P. dolorosa, P. fraudulenta, P. fryxelliana, P. fukuyoi, P. galaxiae, P. granii, P. hallegraeffii, P. hasleana, P. heimii, P. inflatula, P. kodamae, P. limii, P. linea, P. lineola, P. lundholmiae, P. mannii, P. micropora, P. multiseries, P. multistrata, P. nanaoensis, P. obtuse, P. plurisecta, P. prolongatoides, P. pseudodelicatissima, P. pungens, P. pungiformis, P. roundii, P. sabit, P. striata, P. sinica, P. simulans, P. subcurvata, P. subfraudulenta, P. subpacifica, P. turgidula, P. turgiduloides*, or another *Pseudo-nitzschia* species. In still another aspect, the algae and/or diatoms can be a *Thalassiosira* species such as, for example, *T. aestivalis, T. allenii, T. ambigua, T. andamanica, T. angstii, T. angulate, T. anguste-lineata, T. antarctica, T. antiqua, T. autraliensis, T. australis, T. baldaufii, T. baltica, T. binate, T. bioculata, T. bipartite, T. bipora, T. bramaputrae, T. brunii, T. bulbosa, T. burckliana, T. calfornica, T. cardiophora, T. cedarkeyensis, T. centra, T. complicate, T. concaviuscula, T. conferta, T. constricta, T. coronifera, T. curviseriata, T. delicate, T. delicatula, T. depressa, T. dichotomica, T. diporocyclus, T. dubiosa, T. duostra, T. eccentric, T. echinata, T. elliptipora, T. endoseriata, T. exceptiuncula, T. exigua, T. fasciculate, T. faurii, T. ferelineata, T. flexuosa, T. fraga, T. fragilis, T. frenguellii, T. frenguelliopsis, T. fryxelliae, T. gerloffii, T. gersondei, T. gessneri, T. gracilis, T. gravida, T. grunowii, T. hasleae, T. hendeyi, T. hibernalis, T. hyaline, T. hydra, T. hyperborean, T. ignota, T. incerta, T. inlandica, T. insigna, T. intrannula, T. inura, T. irregulata, T. jouseae, T. kanayae, T. kolbei, T. kushirensis, T. labimarginata, T. lacustris, T. latimarginata, T. lentiginosa, T. leptopus, T. levanderi, T. lineata, T. lineoides, T. lundiana, T. lusca, T. maculate, T. mahoodii, T. makarovae, T. mala, T. margaritae, T. mediaconvexa, T. mediterranea, T. minima, T. minuscula, T. miocenica, T. mioplicata, T. moholensis, T. multipora, T. nana, T. nodulolineata, T. nordenskioeldii, T. oceanica, T. oliveriana, T. oranica, T. ornate, T. pacifica, T. partheneia, T. parva, T. patagonica, T. perispinosa, T. perpusilla, T. planiuscula, T. plicata, T. plicatoides, T. poroirregulata, T. poroseriata, T. praefraga, T. praenidulus, T. praeyabei, T. primalabiata, T. profunda, T. proschkinae, T. pseudonana, T. punctigera, T. ritscheri, T. rosulata, T. rotula, T. rudolfi, T. sackettii, T. salvadoriana, T. sancettae, T. scotia, T. simonsenii, T. simplex, T. strelnikovae, T. striata, T. subsalina, T. subtilis, T. symbolophora, T. symmetrica, T. tealata, T. temperi, T. tenera, T. tetrostrupii, T. thalindica, T. transitoria, T. trifulta, T. tubifera, T. tumida, T. umaoiensis, T. urahoroensis, T. variantia, T. visurgis, T. vulnifica, T. webbii, T. yabei*, or another *Thalassiosira* species.

In another aspect, the microorganisms can be cyanobacteria. In one aspect, the cyanobacteria are a Synechococcus species such as, for example, *S. ambiguous, S. arcuatus* var *calcicolus, S. bigranulatus, S. brunneolus, S. caldarius, S. capitatus, S. carcerarius, S. elongates, S. endogloeicus, S. epigloeicus, S. ferruginosus, S. intermedius, S. koidzumii, S. lividus, S. marinus, S. minutissimus, S. mundulus, S. nidulans, S. rayssae, S. rhodobaktron, S. roseo-persicinus, S. roseo-purpureus, S. salinarum, S. salinus, S. sciophilus, S. sigmoideus, S. spongiarum, S. subsalsus, S. sulphuricus, S. vantieghemii, S. violaceus, S. viridissimus, S. vulcanius, S.* sp. PCC7002, *S.* sp. PCC6908, *S.* sp. PCC7942, *S.* sp. WH8101, or *S.* sp. PCC6031. In yet another aspect, the cyanobacteria are a *Trichodesmium* species such as, for example, *T. erythraeum, T. thiebautii, T. hildebrantii, T. contortum, T. tenue*, or *T. radians*. In an alternative aspect, the cyanobacteria are an *Anabaena* species such as, for example, *A. catenula, A.* sp. PCC6411, *A.* sp. PCC7120, *A. variabilis, A. cylindrica, A. cylindrica Lemm* 7122, or *A. cylindrica Lemm* 1611. In still another aspect, the cyanobacteria can be *Oscillatoria tenuis, Microcystis aeruginosa, Anacystis nidulans, Gloeocapsa alipcola*, or *Aphanizomenon flos-aquae*.

In some aspects, the microorganisms can be thermophilic or thermotolerant bacteria. In one aspect, the thermophilic and/or thermotolerant bacteria can be *Sulfolobus* species such as, for example, *S. acidocaldarius* 98-3, *S. solfataricus, S.* sp. B6-2, *S. brierleyi*, or *S. acidocaldarius*. In another aspect, the thermophilic or thermotolerant bacteria can be *Pseudomonas putida, Rhodococcus jostii, Ralstonia* sp. U2, *Sphingomonas* sp. KA1, *Mycobacterium tuberculosis, Terrabacter* sp. DBF63, *Rhodococcus* sp. P200, *Rhodococcus erythropolis, Pseudomonas* sp. XLDN4-9, or *Pseudomonas aeruginosa*. In some aspects, the thermophilic and/or thermotolerant bacteria can be *Anaerolinea thermophila, Caldilinea aerophila, Roseiflexus castenholzii, Roseiflexus* sp. *RS*-1, *Sphaerobacter thermophilus*, or *Thermomicrobium roseum*. In one aspect, the thermophilic or thermotolerant bacteria can be a *Meiothermus* species such as, for example, *M. cerbereus, M. chliarophilus, M. ruber, M. rufus, M. Silvanus*, or *M. timidus*. In another aspect, the thermophilic or thermotolerant bacteria can be a *Thermus* species such as, for example, *T. igniterrae, T. oshimai, T. scotoductus, T.* sp. CCB_US3_UF1, or *T. thermophilus*. In still another aspect, the thermophilic or thermotolerant bacteria can be an *Alicyclobacillus* species such as, for example, *A. acidocaldarius, A. acidoterrestris, A. hesperidum*, or *A. pomorum*. In one aspect, the thermophilic or thermotolerant bacteria can be a *Thermotoga* species such as, for example, *T. maritime,*

*T. naphthophila, T.* sp. Mc24, *T.* sp. RQ2, or *T.* sp. Xyl54. In one aspect, the thermophilic or thermotolerant bacteria can be *Bacillus thermotolerans, Brevibacillus thermoruber, Cohnella thermotolerans, Coprothermobacter platensis, Geobacillus* sp. *JF*8, *Geobacillus thermoglucosidasus, Sulfobacillus thermosulfdooxidans, Thermoactinomycetaceae* sp. GD1, *Thermoanaerobacterium xylanolyticum, Fervidobacterium pennivorans*, or *Thermosipho africanus.*

In some aspects, the microorganisms can be chemoautotrophic bacteria. In one aspect, the chemoautotrophic bacteria can be a species such as, for example, *Hydrogenovibrio crunogenus*. In another aspect, the chemoautotrophic bacteria can be methanogens. In one aspect, the methanogens can be *Methanobacterium bryantii, Methanobacterium formicum, Methanobrevibacter arboriphilicus, Methanobrevibacter gottschalkii, Methanobrevibacter ruminatium, Methanobrevibacter smithii, Methanococcus chunghsingensis, Methanococcus burtonii, Methanococcus aeolicus, Methanococcus deltae, Methanococcus jannaschii, Methanococcus maripaludis, Methanococcus vannielli, Methanocorpusculum labreanum, Methanoculleus bourgensis, Methanoculleus marisnigri, Methanoflorens stordalenmirensis, Methanofolis liminatans, Methanogenium cariaci, Methanogenium frigidum, Methanogenium organophilum, Methanogenium wolfei, Methanomicrobium mobile, Methanopyrus kandleri, Methanoregula boonei, Methanosaeta concilii, Methanosaeta thermophila, Methanosarcina acetivorans, Methanosarcina barkeri, Methanosarcina mazei, Methanosphaera stadtmanae, Methanospirillum hungatei, Methanothermobacter defluvii, Methanothermobacter thermoautotrophicus, Methanothermobacter thermoflexus, Methanothermobacter wolfei, Methanothrix sochgenii*. In another aspect, the chemoautotrophic bacteria can be a *Nitrosomonas* species such as, for example, *N. aestuarii, N. communis, N. europaea, N. eutropha, N. halophila, N. marina, N. nitrosa, N. oligotropha, N. stercoris*, or *N. ureae.*

In one aspect, the microorganisms can be a chemolithotrophic species. In a further aspect, the chemolithotrophic species can be bacteria such as, for example, *Carboxydothermus hydrogenoformans*. In another aspect, the chemolithotrophic species can be archaea such as, for example, an *Archaeoglobus* species, e.g., *A. fulgidus, A. lithotrophicus, A. infectus, A. profundus*, or *A. veneficus*, or another archaea species such as, for example, *Thermocladium modesties* or *Caldivirga maquillingensis*. In yet another aspect, the chemolithotrophic species can be a sulfur-reducing bacterium. In one aspect, the sulfur-reducing bacterium is a *Desulfotomaculum* species such as, for example, *D. acetoxidans, D. aeronauticum, D. alcoholivorax, D. alkaliphilum, D. antarcticum, D. arcticum, D. australicum, D. carboxydivorans, D. defluvii, D. geothermicum, D. gibsoniae, D. guitoideum, D. halophilum, D. hydrothermale, D. intricatum, D. kuznetsovii, D. luciae, D. nigrificans, D. peckii, D. putei, D. ruminis, D. sapomandens, D. solfataricum, D. thermoacetoxidans, D. thermobenzoicum, D. thermocisternum, D. thermosapovorans, D. thermosubterraneum, D. tongense*, or *D. varium*. In one aspect, the sulfur-reducing bacterium is *Desulfosporomusa polytropa* or *Thiobacillus denitrificans*. In yet another aspect, the sulfur-reducing bacterium is a *Desulfosporosinus* species such as, for example, *D. acididurans, D. acidiphilus, D. auripigmenti, D. burensis, D. hippie, D. lacus, D. meridiei, D. orientis*, or *D. youngiae.*

In one aspect, the microorganisms are purple sulfur bacteria such as, for example, species from any of the following genera: *Allochromatium, Amoebobacter, Chromatium, Halochromatium, Isochromatium, Lamprobacter, Lamprocystis, Marichromatium, Nitrosococcus, Pfenniga, Rhabdochromatium, Rheinheimera, Thermochromatium, Thioalkalicoccus, Thiobaca, Thiocaspa, Thiococcus, Thiocystis, Thiodictyon, Thioflavicoccus, Thiohalocapsa, Thiolamprovum, Thiopedia, Thiophaeococcus, Thiorhodococcus, Thiorhodovibrio, Thiospirillum, Acidihalobacter, Alkalalimnicola, Alkalispirillum, Aquisalimonas, Arhodomonas, Ectothiorhodosinus, Ectothiorhodospira, Halorhodospira, Natronocella, Nitrococcus, Nitrospira, Nitrobacter, Nitrospina, Thioalkalispira, Thioalkalivibrio, Thiolahospira, Thiorhodospira, Thioalkalibacter*, or *Guyparkeria*. In another aspect, the microorganisms are *Halothiobacillus kellyi, Halothiobacillus neapolitanus, Nitrospira moscoviensis*, or *Nitrospira marina*. In yet another aspect, the microorganisms are a *Nitrosomonas* species such as, for example, *N. aestuarii, N. communis, N. europaea, N. eutropha, N. halophila, N. marina, N. nitrosa, N. oligotropha, N. stercoris*, or *N. ureae*. In still another aspect, the microorganisms are *Nitrobacter* species such as, for example, *N. alkalicus, N. hamburgensis, N. vulgaris*, or *N. winogradskyi.*

In some aspects, the microorganisms are actinomycetes. In one aspect, the actinomycetes are *Mycobacterium* species such as, for example, *M. tuberculosis, M. africanum, M. bovis, M. canetti, M. caprae, M. microti, M. mungi, M. orygis, M. pinnipedii, M. suricattae, M. avium, M. avium paratuberculosis, M. avium silvaticum, M. avium hominissuis, M. colombiense, M. indicus pranii, M. intracellulare, M. asiaticum, M. gordonae, M. gastri, M. kansasii, M. hiberniae, M. icosiumassiliensis, M. nonchromogenicum, M. terrae, M. trivial, M. ulcerans, M. pseudoshottsii, M. shottsii, M. florentinum, M. genavense, M. heidelbergense, M. interjectum, M. kubicae, M. lentiflavum, M. montefiorense, M. palustre, M. parascrofulaceum, M. simiae, M. triplex, M. arabiense, M. aromaticivorans, M. aquaticum, M. bacteremicum, M. bohemicum, M. botniense, M. branderi, M. celatum, M. chimaera, M. conspicuum, M. cookie, M. doricum, M. farcinogenes, M. haemophilum, M. heckeshornense, M. intracellulare, M. lacus, M. leprae, M. lepraemurium, M. lepromatosis, M. liflandii, M. llatzerense, M. malmoense, M. marinum, M. neoaurum, M. monacense, M. murale, M. nebraskense, M. saskatchewanense, M. sedimins, M. scrofulaceum, M. shimoidei, M. szulgai, M. talmoniae, M. tusciae, M. xenopi, M. yongonense, M. intermedium, M. abscessus, M. bollettii, M. massiliense, M. chelonae, M. immunogenum, M. stephanolepidis, M. boenickei, M. brisbanense, M. cosmeticum, M. fortuitum, M. fortuitum* subsp. *Acetamidolyticum, M. houstonense, M. mageritense, M. neworleansense, M. peregrinum, M. porcinum, M. senegalense, M. septicum, M. aubagnese, M. mucogenicum, M. phocaicum, M. austroafricanum, M. diernhoferi, M. frederiksbergense, M. hodleri, M. neoaurum, M. parafortuitum, M. aurum, M. vaccae, M. chitae, M. fallax, M. agri, M. aichiense, M. alvei, M. arupense, M. barrassiae, M. brumae, M. canariasense, M. chubuense, M. conceptionense, M. confluentis, M. duvalii, M. elephantis, M. flavescens, M. gadium, M. gilvum, M. hossiacum, M. holsaticum, M. iranicum, M. kosmossense, M. madagascariense, M. massilipolynesiensis, M. moriokaense, M. obuense, M. phlei, M. psychrotolerans, M. pulbveris, M. pyrenivorans, M. smegmatis, M. goodie, M. wolinskyi, M. sphagni, M. thermoresistibile, M. vanbaalenii, M. arosiense, M. aubagnense, M. chlorophenolicum, M. fluoroanthenivorans, M. kumamotonense, M. novacastrense, M. parmense, M. poriferae, M. rhodesiae, M. seoulense*, or *M. tokaiense.*

In another aspect, the actinomycetes can be a *Rubrobacter* species such as, for example, *R. aplysinae, R. bracarensis, R. calidifluminis, R. naiadicus, R. radiotolerans, R. taiwanensis, R. xylanophilus*, or *R. wessexii*. In a further aspect, the actinomycetes can be a *Frankia* species such as, for example, *F. alni, F. asymbiotica, F. californensis, F. casuarinae, F. coriariae, F. datiscae, F. discariae, F. elaeagni*, or *F. inefficax*. In still another aspect, the actinomycetes can be a *Sanguibacter* species such as, for example, *S. antarcticus, S. inulinus, S. keddieii, S. marinus, S. soli*, or *S. suarezii*. In one aspect, the actinomycetes can be *Rarobacter faecitabidus, Rarobacter incanus, Jonesia denitrificans, Jonesia quinghaiensis, Varibaculum anthropi, Varibaculum cambriense, Varibaculum timonense*, or *Actinotignum suis*.

In still another aspect, the actinomycetes can be an *Actinomyces* species such as, for example, *A. bovis, A. bowdenii, A. canis, A. cardiffensis, A. catuli, A. coleocanis, A. dentalis, A. denticolens, A. europaeus, A. funkei, A. georgiae, A. gerencseriae, A. graevenitzii, A. hongkongensis, A. hordeovulneris, A. howellii, A. humiferus, A. hyovaginalis, A. israelii, A. marimammalium, A. meyeri, A. naeslundii, A. nasicola, A. neuii, A. odontolyticus, A. oricola, A. radicidentis, A. radingae, A. slackii, A. streptomycini, A. suimastitidis, A. suis, A. turicensis, A. urogenitalis, A. vaccimaxillae*, or *A. viscosus*.

In yet another aspect, the actinomycetes can be selected from *Arcanobacterium* species such as, for example, *A. abortisuis, A. bernardiae, A. bialowiezense, A. bonsai, A. canis, A. hamolyticum, A. hippocolae, A. phocae, A. phocisimile, A. pinnipediorum, A. pluranimalium*, or *A. pyogenes*. In one aspect, the actinomycetes can be selected from among *Demequina* species such as, for example, *D. activiva, D. aestuarii, D. aurantiaca, D. globuliformis, D. litorisediminis, D. lutea, D. oxidasica, D. salsinemoris*, or *D. sediminicola*. In still another aspect, the actinomycetes can be selected from *Lysinimicrobium* species such as, for example, *L. aestuarii, L. flavum, L. gelatinilyticum, L. iriomotense, L. luteum, L. mangrove, L. pelophilum, L. rhisosphaerae, L. sediminis, L. soli*, or *L. subtropicum*.

In another aspect, the actinomycetes are selected from *Brevibacterium* species such as, for example, *B. acetyliticum, B. albidum, B. antiquum, B. aurantiacum, B. avium, B. casei, B. celere, B. divaricatum, B. epidermidis, B. frigoritolerans, B. halotolerans, B. immotum, B. iodimum, B. linens, B. luteolum, B. luteum, B. mcbrellneri, B. otitidis, B. oxydans, B. paucivorans, B. permense, B. picturae, B. samyangense, B. sanguinis*, or *B. stationis*. In an alternative aspect, the actinomycetes are selected from *Corynebacterium* species such as, for example, *C. accolens, C. afermentans, C. alimapuense, C. ammoniagenes, C. amycolatum, C. argentoratense, C. aquaticum, C. auris, C. bovis, C. diphtheria, C. equi, C. efficiens, C. flavescens, C. glucuronolyticum, C. glutamicum, C. granulosum, C. haemolyticum, C. halofitica, C. kroppenstedtii, C. jeikeium, C. macginleyi, C. matruchotii, C. minutissimum, C. mucifaciens, C. parvum, C. paurometabolum, C. propinquum, C. pseudodiphtheriticum, C. pseudotuberculosis, C. ovis, C. pyogenes, C. urealyticum, C. renale, C. resistens, C. spec, C. striatum, C. tenuis, C. ulcerans, C. urealyticum, C. uropygiale*, or *C. xerosis*. In still another aspect, the actinomycetes are selected from among *Nocardia* species such as, for example, *N. aerocolonigenes, N. Africana, N. argentinensis, N. asteroids, N. blackwellii, N. brasiliensis, N. brevicatena, N. carnea, N. cerradoensis, N. corallina, N. cyriacigeorgica, N. dassonvillei, N. elegans, N. farcinica, N. ignorata, N. nigiitonsis, N. nova, N. opaca, N. otitidis-cavarium, N. paucivorans, N. pseudobrasiliensis, N. rubra, N. seriolae, N. transvelencesis, N. uniformis, N. vaccinii*, or *N. veteran*. In one aspect, the actinomycetes are selected from *Rhodococcus* species such as, for example, *R. aerolatus, R. aetherivorans, R. agglutinans, R. aurantiacus, R. artemisiae, R. baikonurensis, R. biphenylivorans, R. boritolerans, R. equi, R. canchipurensis, R. cerastii, R. cercidiphylli, R. coprophilus, R. corynebacterioides, R. defluvii, R. electrodiphilus, R. enclensis, R. erythropolis, R. fascians, R. globerulus, R. gordoniae, R. hoagie, R. imtechensis, R. jialingiae, R. jostii, R. koreensis, R. kroppenstedtii, R. kummingensis, R. kyotoensis, R. maanshanensis, R. marinonascens, R. nanhaiensis, R. olei, R. opacus, R. percolates, R. phenolicus, R. polyvorum, R. pyridinivorans, R. gingshengii, R. rhodochrous, R. rhodnii, R. ruber, R. jostii, R. soli, R. triatomae, R. trifolii, R. tukisamuensis, R. wratislaviensis, R. yuannanensis*, or *R. zopfii*.

In one aspect, the actinomycete can be a *Kineococcus* species such as, for example, *K. aurantiacus, K. endophytica, K. glutinatus, K. gynurae, K. gypseus, K. radiotolerans, K. rhizosphaerae, K. tegulae*, or *K. xinjiangensis*. In another aspect, the actinomycete is selected from among *Nakamurella* species such as, for example, *N. endophytica, N. flavida, N. lacteal, N. multipartita*, or *N. panacisegetis*. In still another aspect, the actinomycete is *Haloactinopolyspora alba* or *Haloactinopolyspora aklaliphila*. In still another aspect, the actinomycete is a *Jiangella* species such as, for example, *J. ginsengisoli, J. mangrove, J. gansuensis, J. aklaliphila, J. muralis*, or *J. alba*. In yet another aspect, the actinomycete is *Phytoactinopolyspora endophytica* or *Phytoactinopolyspora alkaliphila*.

In one aspect, the actinomycete is *Stackebrandia albivlava, Stakebrandia nassauensis*, or *Haloglycomyces albus*. In another aspect, the actinomycete is a *Glycomyces* species such as, for example, *G. tenuis, G. arizonensis, G. halotolerans, G. albus, G. fuscus, G. tarimensis, G. artemisiae, G. mayteni, G. sambucus, G. scopariae, G. harbinensis, G. endophyticus, G. algeriensis, G. lechevalierae*, or *G. rutgersensis*. In yet another aspect, the actinomycete is *Actinocorallia herbida, Bogoriella caseilytica*, or a *Georgenia* species such as, for example, *G. deserti, G. ferrireducens, G. soli, G. muralis, G. halophila, G. ruanii*, or *G. thermotolerans*.

In one aspect, the actinomycete is selected from *Thermotunica guangxiensis, Goodfellowiella coeruleoviolacea, Umezawaea tangerine, Lechevalieria fradiae, Lechevalieria nigeriaca, Lechivalieria flava, Actinokineospora soli, Labedaea rhizosphaerae, Longimycelium tulufanense, saccharopolyspora cebuensis, Saccharopolyspora rectivirgula, Halopolyspora alba, Sciscionella marina, Yuhushiella deserti*, or *Haloechinothrix alba*. In another aspect, the actinoycete is selected from *Spirilliplanes yamanashiensis, Xiangella phaseoli, Verrucosispora qiuiae, Polymorphospora rubra, Micromonospora avicenniae, Actinaurispora siamensis, Jishengella endophytica, Catellatospora bangladeshensis, Allocatelliglobosispora scoriae, Catelliglobosispora koreensis, Rhizocola hellebore, Couchioplanes caeruleus azureus, Couchioplanes caeruleus caeruleus, Pseudosporangium ferrugineum*, or *Krasilnikovia cinnamomea*. In a further aspect, the actinomycete can be selected from *Arthrobacter echigonensis, Auritidibacter ignavus, Cellulosimicrobium cellulans, Cellulosimicrobium funkei, Cellulosimicrobium terreum, Isoptericola chiayiensis, Isoptericola jiangsuensis, Isoptericola dokdonensis, Isoptericola halotolerans, Isoptericola hypogeus, Isoptericola variabilis, Xylanimonas cellulosilytica, Xylanimicrobium pachnodae, Xylanimicrobium ulmi, Myceligenerans crystallogenes, Myceligenerans halotolerans, Myceligenerans xiligouense*, or a *Promicromonospora* species such as, for example, *P. cymbopogonis, P. citrea, P. kroppenstedtii, P. umidemergens, P. sukumoe, P. aerolata*, or *P. vindobonensis*.

In one aspect, the actinomycete is a *Candidatus* species such as, for example, *C. aquiluna rubra, C. flaviluna lacus, C. limnoluna rubra, C. planktoluna difficilis*, or *C. rhodoluna*. In another aspect, the actinomycete is selected from *Crocebacterium ilecola, Cryocola antiques, Humibacter albus, Schumannella luteola, Chryseoglobus frigidaquae, Leifsonia kribbensis, Leifsonia kafniensis, Phycicola gilvus, Leifsonia pindariensis, Microterricola viridarii, Leifsonia bigeumensis, Leifsonia antarctica, Glaciibacter superstes, Marisediminicola antarctica, Frigoribacterium faeni, Yonghaparkia alkaliphila, Clavibacter michiganensis, Frigoribacterium mesophilum, Klugiella xanthotipulae, Cryobacterium mesophilum, Amnibacterium kyonggiense, Labedella gwakjiensis*, or *Okibacterium fritillariae.*

In one aspect, the actinomycete is selected from *Nostocoida aromativora, Kribbia dieselivorans, Janibacter melonis, Marihabitans asiaticum, Mobilicoccus Pelagius, Dermatophilis congolensis, Pisciocccus intestinalis, Kineosphaera limosa, Austwickia chelonae, Yimella lutea, Branchiibius hedensis, Luteipulveratus mongoliensis, Demetria terragena, Fodinibacter luteus, Ornithinibacter aureus, Lapillicoccus jejuensis, Ornithinicoccus hortensis, Oryzihumus leptocrescens, Intrasporangium calvum, Humihabitans oryzae, Humibacillus xanthopallidus, Terrabacter aeriphilus, Teracoccus luteus, Fodinicola feengrottensis*, or a *Cryptosporangium* species such as, for example, *C. arvum, C. japonicum, C. aurantiacum*, or *C. minutisporangium*. In another aspect, the actinomycete is a *Blastococcus* species such as, for example, *B. saxobsidens, B. aggregates, B. endophyticus*, or *B. jejuensis*. In still another aspect, the actinomycete is a *Modestobacter* species such as, for example, *M. multiseptatus, M. versicolor, M. marinus*, or *M. roseus*. In yet another aspect, the actinonycete is a *Geodermatophilus* species such as, for example, *G. terrae, G. soli, G. taihuensis, G. ruber, G. siccatus, G. africanus, G. obscures, G. arenarius, G. nigrescens, G. amargosae, G. normandii, G. saharensis, G. telluris*, or *G. tzadiensis*. In a further aspect, the actinomycete is selected from *Aciditerrimonas ferrireducens, Ferrithrix thermotolerans, Acidimicrobium ferroxidans, Ferrimicrobium acidiphilum, Iamia majanohamensis, Aquihabitans daechungensis, Illumatobacter fluminis, Illumatobacter coccineus*, or *Illumatobacter nonamiensis.*

In another aspect, the actinomycete is an *Atopobium* species such as, for example, *A. parvulum, A. rimrae, A. fossor, A. minutum*, or *A. vaginae*. In an alternative aspect, the actinomycete is an *Olsenella* species such as, for example, *O. profuse, O. umbonata, O. uli*. In yet another aspect, the actinomycete is a *Collinsella* species including, but not limited to, *C. tanakaei, C. aerofaciens, C. intestinalis*, or *C. stercoris*. In another aspect, the actinomyete is selected from *Coriobacterium glomerans, Cryptobacterium curtum, Gordonibacter pamelaeae, Paraeggerthella hongkongensis, Eggerthella lenta, Eggerthella sinensis, Denitrobacterium detoxificans, Adlercreutzia equolifaciens, Asaccharobacter celatus, Enterorhabdus caecimuris*, or *Enterorhabdus mucosicola*. In still another aspect, the actinomycete is a *Slackia* species such as, for example, *S. isoflavoniconvertens, S. exigua, S. heliotrinitrireducens, S. equolifaciens, S. faecicanis*, or *S. piriformias.*

In one aspect, the actinomycete is a *Kitasatospora* species including, but not limited to, *K. arboriphila, K. azatica, K. cheerisanensis, K. cineracea, K. cochleata, K. cystarginea, K. gansuensis, K. griseola, K. Kifunensis, K. mediocidica, K. niigatensis, K. nipponensis, K. paracochleata, K. paranensis, K. phosalacinea, K. putterlickiae, K. sampliensis, K. setae, K. terrestris, K. viridifaciens*, or *K. viridis.*

In another aspect, the actinomycete is a *Streptomyces* species such as, for example, *S. abietis, S. abikoensis, S. aburaviensis, S. achromogenes, S. acidiscabies, S. actinomycinicus, S. acrimycini, S. actuosus, S. aculeolatus, S. adustus, S. abyssalis, S. afghaniensis, S. aidingensis, S. africanus, S. alanosinicus, S. albaduncus, S. albiaxialis, S. albidochromogenes, S. albiflavescens, S. albiflaviniger, S. albidoflavus, S. albofaciens, S. alboflavus, S. albogriseolus, S. albolongus, S. alboniger, S. albospinus, S. albulus, S. albus, S. aldersoniae, S. alfalfa, S. alkalkphilus, S. alkalithermotolerans, S. almquistii, S. alni, S. althioticus, S. amakusaensis, S. ambofaciens, S. amphotericinicus, S. amritsarensis, S. anandii, S. andamanensis, S. angustmyceticus, S. anthocyanicus, S. antibioticus, S. antimycoticus, S. anulatus, S. aomiensis, S. araujoniae, S. ardus, S. aridus, S. arenae, S. armeniacus, S. artemisiae, S. arcticus, S. ascomycinicus, S. asenjonii, S. asiaticus, S. asterosporus, S. atacamensis, S. atratus, S. atriruber, S. atroolivaceus, S. atrovirens, S. aurantiacus, S. aurantiogriseus, S. auratus, S. aureocirculatus, S. aureofaciens, S. aureorectus, S. aureoverticillatus, S. aureus, S. avellaneus, S. avermitilis, S. avicenniae, S. avidinii, S. axinellae, S. azureus, S. bacillaris, S. badius, S. bambergiensis, S. bambusae, S. bangladeshensis, S. baliensis, S. barkulensis, S. beijiangensis, S. bellus, S. bikiniensis, S. blastmyceticus, S. bluensis, S. bobili, S. bohaiensis, S. boninensis, S. bottropensis, S. brasiliensis, S. brevispora, S. bullii, S. bungoensis, S. burgazadensis, S. bryophytorum, S. cacaoi, S. caelestis, S. caeruleatus, S. caldifontis, S. caldiresistens, S. calvus, S. camponoticapitis, S. canalis, S. canaries, S. canchipurensis, S. candidus, S. cangkringensis, S. caniferus, S. canus, S. capparidis, S. capillispiralis, S. capoamus, S. carpaticus, S. carpinensis, S. castelarensis, S. catbensis, S. catenulae, S. cavourensis, S. cellostaticus, S. celluloflavus, S. cellulolyticus, S. cellulosae, S. capitiformicae, S. cerasinus, S. chartreusis, S. chattanoogensis, S. cheonanensis, S. chiangmaiensis, S. chitinivorans, S. chrestomyceticus, S. chromofuscus, S. chryseus, S. chilikensis, S. chlorus, S. chumphonensis, S. cinereorectus, S. cinereoruber, S. cinereospinus, S. cinereus, S. cinerochromogenes, S. cinnabarinus, S. cinnabarigriseus, S. cinnamonensis, S. cinnamoneus, S. cirratus, S. ciscaucasicus, S. clavifer, S. clavuligerus, S. coacervatus, S. cocklensis, S. coelescens, S. coelicoflavus S. coelicolor, S. coeruleoflavus, S. coeruleofuscus, S. coeruleoprunus, S. coerulerubidus, S. coerulescens, S. collinus, S. colombiensis, S. corchorusii, S. costaricanus, S. cremeus, S. crystallinus, S. cuspidosporus, S. cyaneofuscatus, S. cyaneus, S. cyanoalbus, S. cyslabdanicus, S. daghestanicus, S. daliensi, S. gaqingensis, S. davaonensis, S. deccanensis, S. decoyicus, S. demainii, S. deserti, S. diastaticus, S. diastatochromogenes, S. djakartensis, S. drozdowiczii, S. durhamensis, S. durmitorensis, S. echinatus, S. echinoruber, S. ederensis, S. emeiensis, S. endophyticus, S. endus, S. enissocaesilis, S. erythrogriseus, S. erringtonii, S. eurocidicus, S. europaeiscabiei, S. eurythermus, S. exfoliates, S. fabae, S. fenghuangensis, S. ferralitis, S. filamentosus, S. fildesensis, S. filipinensis, S. fimbriatus, S. finlayi, S. flaveolus, S. flaveus, S. flavofungini, S. flavotricini, S. flavovariabilis, S. flavovirens, S. flavoviridis, S. formicae, S. fractus, S. fradiae, S. fragilis, S. fukangensis, S. fulvissimus, S. fulvorobeus, S. fumanus, S. fumigatiscleroticus, S. fuscichromogenes, S. fuscigenes, S. galbus, S. galilaeus, S. gamaensis, S. gancidicus, S. gardneri, S. gelaticus, S. geladnamycininus, S. geysiriensis, S. ghanaensis, S. gilvifuscus, S. glaucescens, S. glauciniger, S. glaucosporus, S. glaucus, S. globisporus, S. globosus, S. glomeratus, S. glomeroaurantiacus, S. glycovorans, S. gobitricini, S. goshikiensis, S. gougerotii, S. graminearus, S. gramineus, S. graminifolii, S.*

*graminilatus, S. graminisoli, S. griseiniger, S. griseoaurantiacus, S. griseocarneus, S. griseochromogenes, S. griseoflavus, S. griseofuscus, S. griseoincarnatus, S. griseoloalbus, S. griseolus, S. griseoluteus, S. griseomycini, S. griseoplanus, S. griseorubens, S. griseoruber, S. griseorubiginosus, S. griseosporeus, S. griseostramineus, S. griseoviridis, S. griseus, S. guanduensis, S. gulbargensis, S. hainanensis, S. haliclonae, S. halophytocola, S. halstedii, S. harbinensis, S. hawaiiensis, S. hebeiensis, S. heilongjiangensis, S. heliomycini, S. helvaticus, S. herbaceous, S. herbaricolor, S. himastatinicus, S. hiroshimensis, S. hirsutus, S. hokutonensis, S. hoynatensis, S. humidus, S. humiferus, S. hundungensis, S. hyaluromycini, S. hyderabadensis, S. hygroscopicus, S. hypolithicus, S. iakyrus, S. iconiensis, S. incanus, S. indiaensis, S. indigoferus, S. indicus, S. indoligenes, S. indonesiensis, S. intermedius, S. inusitanus, S. ipomoeae, S. iranensis, S. janthinus, S. javensis, S. jeddahensis, S. jietaisiensis, S. jiujiangensis, S. kaempferi, S. kanamyceticus, S. karpasiensis, S. kasugaensis, S. katrae, S. kalpinensis, S. kebangsaanensis, S. klenkii, S. koyangensis, S. kunmingensis, S. kurssanovii, S. kronopolitis, S. krungchingensis, S. labedae, S. lacrimifluminis, S. lactacystinicus, S. lacticiproducens, S. ladulatispora, S. lanatus, S. lannensis, S. lasiicapitis, S. lateritius, S. laurentii, S. lavendofoliae, S. lavendulae, S. lavenduligriseus, S. leeuwenhoekii, S. lavendulocolor, S. levis, S. libani, S. lienomycini, S. lilacinus, S. lincolnensis, S. litmocidini, S. litoralis, S. lohii, S. lomondensis, S. longisporoflavus, S. longispororuber, S. lopnurensis, S. lonarensis, S. longisporus, S. longwoodensis, S. lucensis, S. lunaelactis, S. lunalinharesii, S. luridiscabei, S. luridus, S. lusitanus, S. lushanensis, S. luteireticuli, S. luteogriseus, S. luteosporeus, S. luteus, S. lydicus, S. macrospores, S. malachitofuscus, S. malachitospinus, S. malaysiensis, S. mangrove, S. marinus, S. marokkonensis, S. mashuensis, S. massaporeus, S. matensis, S. mayteni, S. mauvecolor, S. megaspores, S. melanogenes, S. melanosporofaciens, S. mexicanus, S. michiganensis, S. microflavus, S. milbemycinicus, S. minutiscleroticus, S. mirabilis, S. misakiensis, S. misionensis, S. mobaraensis, S. monomycini, S. mordarskii, S. morookaense, S. muensis, S. murinus, S. mutabilis, S. mutomycini, S. naganishii, S. nanhaiensis, S. nanshensis, S. narbonensis, S. nashvillensis, S. netropsis, S. neyagawaensis, S. niger, S. nigrescens, S. nitrosporeus, S. niveiciscabiei, S. niveoruber, S. niveus, S. noboritoensis, S. nodosus, S. nogalater, S. nojiriensis, S. noursei, S. novaecaesareae, S. ochraceiscleroticus, S. odonnellii, S. olivaceiscleroticus, S. olivaceoviridis, S. olivaceus, S. olivicoloratus, S. olivochromogenes, S. olivomycii, S. olivoverticillatus, S. omiyaensis, S. osmaniensis, S. orinoci, S. oryzae, S. ovatisporus, S. pactum, S. palmae, S. panacagri, S. panaciradicis, S. paradoxus, S. parvulus, S. parvus, S. pathocidini, S. paucisporeus, S. peucetius, S. phaeochromogenes, S. phaeofaciens, S. phaeogriseichromatogenes, S. phaeoluteichromatogenes, S. phaeoluteigriseus, S. phaeopurpureus, S. pharetrae, S. pharmamarensis, S. phyllanthi, S. phytohabitans, S. pilosus, S. pini, S. platensis, S. plicatus, S. plumbiresistens, S. pluricolorescens, S. pluripotens, S. polyantibioticus, S. polychromogenes, S. polygonati, S. polymachus, S. poonensis, S. prasinopilosus, S. prasinosporus, S. prasinus, S. pratens, S. pratensis, S. prunicolor, S. psammoticus, S. pseudoechinosporeus, S. pseudogriseolus, S. pseudovenezuelae, S. pulveraceus, S. puniceus, S. puniciscabiei, S. purpeofuscus, S. purpurascens, S. purpureus, S. purpurogeneiscleroticus, S. qinglanensis, S. racemochromogenes, S. radiopugnans, S. rameus, S. ramulosus, S. rapamycinicus, S. recifensis, S. rectiviolaceus, S. regensis, S. resistomycificus, S. reticuliscabei, S. rhizophilus, S. rhizosphaericus, S. rhizosphaerihabitans, S. rimosus, S. rishiriensis, S. rochei, S. roietensis, S. rosealbus, S. roseiscleroticus, S. roseofulvus, S. roseolilacinus, S. roseolus, S. roseosporus, S. roseoviolaceus, S. roseoviridis, S. ruber, S. rubidus, S. rubiginosohelvolus, S. rubiginosus, S. rubrisoli, S. rubrogriseus, S. rubrus, S. rutgersensis, S. salilacus, S. samsunensis, S. sanglieri, S. sannanensis, S. sanyensis, S. sasae, S. scabiei, S. scabrisporus, S. sclerotialus, S. scopiformis, S. scopuliridis, S. sedi, S. seoulensis, S. seranimatus, S. seymenliensis, S. shaanxiensis, S. shenzhenensis, S. showdoensis, S. silaceus, S. siamensis, S. similanensis, S. sindenensis, S. sioyaensis, S. smyrnaeus, S. sodiiphilus, S. solisilvae, S. somaliensis, S. sudanensis, S. sparsogenes, S. sparsus, S. specialis, S. spectabilis, S. speibonae, S. speleomycini, S. spinoverrucosus, S. spiralis, S. spiroverticillatus, S. spongae, S. spongiicola, S. sporocinereus, S. sporoclivatus, S. spororaveus, S. sporoverrucosus, S. staurosporininus, S. stelliscabiei, S. stramineus, S. subrutilus, S. sulfonofaciens, S. sulphureus, S. sundarbansensis, S. synnematoformans, S. tacrolimicus, S. tanashiensis, S. tateyamensis, S. tauricus, S. tendae, S. termitum, S. thermoalcalitolerans, S. thermoautotrophicus, S. thermocarboxydovorans, S. thermocarboxydus, S. thermocoprophilus, S. thermodiastaticus, S. thermogriseus, S. thermolineatus, S. thermospinosisporus, S. thermoviolaceus, S. thermovulgaris, S. thinghirensis, S. thioluteus, S. tritici, S. torulosus, S. toxytricini, S. tremellae, S. tritolerans, S. tricolor, S. tsukubensis, S. tubercidicus, S. tuirus, S. tunisiensis, S. turgidiscabies, S. tyrosinilyticus, S. umbrinus, S. variabilis, S. variegates, S. varsoviensis, S. verticillus, S. vastus, S. venezuelae, S. verrucosisporus, S. vietnamensis, S. vinaceus, S. vinaceusdrappus, S. violaceochromogenes, S. violaceolatus, S. violaceorectus, S. violaceoruber, S. violaceorubidus, S. violaceus, S. violaceusniger, S. violarus, S. violascens, S. violens, S. vixens, S. virginiae, S. viridis, S. viridiviolaceus, S. viridobrunneus, S. viridochromogenes, S. viridodiastaticus, S. viridosporus, S. vitaminophilus, S. wedmorensis, S. wellingtoniae, S. werraensis, S. wuyuanensis, S. xanthochromogenes, S. xanthocidicus, S. xantholiticus, S. xanthophaeus, S. xiamenensis, S. xinghaiensis, S. xishensis, S. xylanilyticus, S. yaaensis, S. yanglinensis, S. yangpuensis, S. yanii, S. yatensis, S. yeochonensis, S. yerevanensis, S. yogyakartensis, S. yokosukanensis, S. youssoufiensis, S. yunnanensis, S. zagrosensis, S. zaomyceticus, S. zhaozhouensis, S. zhihengii, S. zinciresistens*, or *S. ziwulingensis.*

II. Organic Component of the Culture Medium

The culture medium used to produce the carbo-ionic extracts described herein includes an organic component. In one aspect, the organic component is composed of water and one or more-carbon-based compounds. In one aspect, the organic component can be a defined medium or an undefined medium. As used herein, an "undefined medium" contains a carbon source, water, various salts, and a source of amino acids and nitrogen and is referred to as an undefined medium because the source of amino acids and nitrogen may be a meat extract (i.e., beef) or a fungal extract (i.e., yeast) containing a variety of compounds that are not fully characterized. An undefined medium may also be called a "non-synthetic" or "chemically undefined" medium. In one aspect, an undefined medium contains at least one component that is not purified, is not completely characterized, and that may not be consistent from batch to batch. In a further aspect, this component can be a partially digested protein. In one aspect, an undefined medium as used herein includes a nutrient broth.

In one aspect, "nutrient broth" contains a yeast extract. In one aspect, a yeast extract can include yeast cells that are allowed to die and decompose, thereby allowing their digestive enzymes to be released and break proteins in the solution down into amino acids and peptides.

In another aspect, nutrient broth contains peptides and casein peptones. "Tryptone" is another word for a subset of casein peptones and, as used herein, is the collection of peptides produced when casein is digested by trypsin. Other peptones and extracts are also contemplated including, but not limited to, gelatin peptones, beef peptones, and beef extracts and other meat extracts. In one aspect, nutrient broth contains casamino acids, which are produced from casein by acid hydrolysis rather than trypsin digestion. In some aspects, nutrient broth contains both tryptone and casamino acids.

In one aspect, beef and other meat extracts can be aqueous extracts of lean tissues. Further in this aspect, beef extract (and by extension, other meat extracts) contains water-soluble substances including, but not limited to, carbohydrates, organic nitrogen compounds, water soluble vitamins, and salts.

By contrast, a "defined medium" contains only chemicals and no yeast, animal-derived extracts or plant extracts. A defined medium may also be called a "synthetic medium" or "chemically defined" medium and is typically prepared from purified ingredients.

In another aspect, the organic component can be "minimal media" (i.e., consisting only of a carbon source, salts to provide trace elements including magnesium, nitrogen, phosphorus, and sulfur, and water). Further in this aspect, minimal media contain only the minimum possible nutrients for colony growth.

In any of the above aspects, the carbon source can be glucose, succinate, or another sugar or carboxylic acid.

In one aspect, the organic component is a nutrient broth that includes water.

In one aspect, the organic component is a nutrient broth that includes sodium chloride in an amount of from 1 g/L to 10 g/L, or from 2.5 g/L to 7.5 g/L, in the amount of about 1, 1.5, 2, 2.5, 3, 3.5, 4, 4.5, 5, 5.5, 6, 6.5, 7, 7.5, 8, 8.5, 9, 9.5, or 10 g/L, where any value can be a lower and upper end-point of a range. In one aspect the amount of sodium chloride is 5.0 g/L of nutrient broth.

In one aspect, the organic component is a nutrient broth that includes a meat extract in the amount of from 0.1 to 5 g/L, or about 0.1, 0.25, 0.5, 0.75, 1, 1.5, 2, 2.5, 3, 3.5, 4, 4.5, or about 5 g/L of meat extract, or contains about 1 g/L of meat extract, where any value can be the upper or lower endpoint of a range.

In one aspect, the organic component is a nutrient broth that includes a yeast extract in the amount of from 0.1 to 5 g/L, or about 0.1, 0.25, 0.5, 0.75, 1, 1.5, 2, 2.5, 3, 3.5, 4, 4.5, or about 5 g/L of yeast extract, or contains about 2 g/L of yeast extract, where any value can be the upper or lower endpoint of a range.

In one aspect, the organic component is a nutrient broth that includes a peptone in the amount of from of from 1 g/L to 10 g/L, or from 2.5 g/L to 7.5 g/L, in the amount of about 1, 1.5, 2, 2.5, 3, 3.5, 4, 4.5, 5, 5.5, 6, 6.5, 7, 7.5, 8, 8.5, 9, 9.5, or 10 g/L, where any value can be the upper or lower endpoint of a range. In one aspect, the amount of peptone is 5.0 g/L of nutrient broth.

In one aspect, the organic component is a nutrient broth that includes water, a meat extract in the amount of from 0.1 to 5 g/L, a yeast extract in the amount of 0.1 to 5 g/L, a peptone in the amount of from 0.1 to 10 g/L, and a salt in the amount of from 0.1 to 10 g/L. In one aspect, the nutrient broth includes water, 1.0 g/L of meat extract, 2.0 g/L of yeast extract, 5.0 g/L of peptone, 5.0 g/L of NaCl, and is adjusted to a final pH of 7.4.

In one aspect, nutrient broth may be commercially available in powdered form or can be a prepared liquid. If provided in powdered form, nutrient broth can be reconstituted by dissolution in distilled water according to instructions from the manufacturer, including a heating step with agitation to completely dissolve the powder. Further in this aspect, nutrient broth is typically sterilized by autoclaving at 121° C. for at least 15 min. In some aspects, the pH of nutrient broth is adjusted after reconstitution.

In some aspects, following preparation, the pH of the nutrient broth can be tested and adjusted with any biocompatible acid, base, or buffer composition. In one aspect, the pH of the nutrient broths useful herein can be from about 6.5 to about 8.5, or can be about 6.5, 7, 7.5, 8, or 8.5. In another aspect, the pH of the nutrient broth useful herein is about 7.4.

III. Inorganic Component of the Culture Medium

The culture medium used to produce the carbo-ionic extracts described herein includes an inorganic component. In one aspect, the inorganic component can include one or more metal salts or other inorganic salts in water. Further in this aspect, the one or more metal or inorganic salts are soluble in the culture medium at the concentrations used, or can be made soluble, or can have their solubility increased, by increasing or decreasing the temperature, pH, or another property of the culture medium, or by modifying several different such properties. In an alternative aspect, changes to the culture medium as a result of microbial growth may allow for higher solubility levels of the salts.

In one aspect, the inorganic component can be a salt of iron, potassium, calcium, magnesium, ammonium, manganese, molybdenum, nickel, zinc, copper, or cobalt salts or any combination thereof. Without wishing to be bound by theory, the inclusion of metal and/or inorganic salts in culture medium can help regulate cell membrane potential, can ensure that necessary enzyme cofactors are present to ensure optimal growth and replication, and can assist with protein and nucleic acid structure formation, among other functions.

In one aspect, the metal and/or inorganic salts can be added to the culture medium individually. In an alternative aspect, the metal and/or inorganic salts can be added as a mixture. In one aspect, the mixture is Wolfe's Mineral Solution.

Iron Salts

In one aspect, the inorganic component includes one or more iron salts. In a further aspect, the one or more iron salts are iron (II) or iron (III) salts. In a still further aspect, the one or more iron salts are selected from ammonium iron (II) sulfate hexahydrate, iron (II) bromide, iron (III) bromide, iron (II) chloride in anhydrous or tetrahydrate form, iron (III) chloride, iron (III) citrate, iron (II) fluoride, iron (III) fluoride in anhydrous or trihydrate form, iron (II) iodide, iron (II) molybdate, iron (III) nitrate nonahydrate, iron (II) oxalate dihydrate, iron (III) phosphate tetrahydrate, iron (III) pyrophosphate, iron (II) sulfate in a hydrate or heptahydrate form, iron (III) sulfate hydrate, and combinations thereof.

In one aspect, the iron salt is present in an amount sufficient to produce a concentration of from 50 to 200 mM of iron ions in the inorganic component prior to mixing with the organic component. In another aspect, the concentration of iron ions is about 50, 60, 70, 80, 90, 100, 110, 120, 130, 140, 150, 160, 170, 180, 190, or about 200 mM, where any number can be the upper or lower endpoint of a range. In still another aspect, the concentration of iron ions in the inorganic component is about 70 mM or is about 175 mM. In one aspect, the iron salt is iron (II) sulfate heptahydrate.

Potassium Salts

In one aspect, the inorganic component includes one or more potassium salts. In a further aspect, the one or more potassium salts are selected from potassium bisulfate, potassium bromide, potassium carbonate, potassium chloride, potassium fluoride, potassium hydroxide, potassium iodide, potassium manganate, potassium molybdate, potassium nitrate, potassium persulfate, dibasic potassium phosphate, monobasic potassium phosphate, potassium pyrophosphate, potassium sulfate, and combinations thereof.

In one aspect, the potassium salt is dibasic potassium phosphate ($K_2HPO_4$) in an amount sufficient to provide a concentration of from 1 to 20 mM of potassium ions in the inorganic component prior to mixing with the organic component. In another aspect, the concentration of potassium ions from dibasic potassium phosphate is about 1, 2, 3, 4, 5, 6, 7, 8, 9, 10, 11, 12, 13, 14, 15, 16, 17, 18, 19, or 20 mM, where any number can be the upper or lower endpoint of a range. In still another aspect, the concentration of potassium ions in the inorganic component from dibasic potassium phosphate is about 4 mM or is about 6 mM.

In one aspect, the potassium salt is potassium chloride in an amount sufficient to provide a concentration of from 0.5 to 5 mM of potassium ions in the inorganic component prior to mixing with the organic component. In another aspect, the concentration of potassium ions from potassium chloride is about 0.5, 1, 1.5, 2, 2.5, 3, 3.5, 4, 4.5, or about 5 mM, where any number can be the upper or lower endpoint of a range. In still another aspect, the concentration of potassium ions in the inorganic component from potassium chloride is about 1 mM to 2 mM. In an alternative aspect, no potassium chloride is added to or included in the inorganic component.

In one aspect, potassium ions in the inorganic component are provided by two or more potassium salts in combination, such as, for example, a combination of dibasic potassium phosphate and potassium chloride sufficient at a concentration of about 1 to about 25 mM of potassium ions in the inorganic component. Further in this aspect, the total concentration of potassium ions in the inorganic component can be about 1, 2, 3, 4, 5, 6, 7, 8, 9, 10, 11, 12, 13, 14, 15, 16, 17, 18, 19, 20, 21, 22, 23, 24, or about 25 mM, where any number can be the upper or lower endpoint of a range. In one aspect, the combined concentration of potassium ions from all potassium salts is about 4 mM or is about 8 mM. In another aspect, additional potassium salts may be used, including those containing other metal ions such as, for example, aluminum. In one aspect, the potassium salt is $AlK(SO_4)_2.2H_2O$.

Calcium Salts

In one aspect, the inorganic component can include one or more calcium salts. In a further aspect, the one or more calcium salts are selected from calcium bromide, calcium carbonate, calcium chloride in an anhydrous or hydrate or hexahydrate form, calcium fluoride, calcium hydroxide, calcium iodide in an anhydrous or hydrate form, calcium nitrate, calcium oxalate, monobasic calcium phosphate, tribasic calcium phosphate, calcium pyrophosphate, calcium sulfate, and combinations thereof.

In one aspect, the calcium salt is present in an amount sufficient to provide a concentration of from 10 to 100 μM of calcium ions in the inorganic component prior to mixing with the organic component. In another aspect, the concentration of calcium ions is about 10, 15, 20, 25, 30, 35, 40, 45, 50, 55, 60, 65, 70, 75, 80, 85, 90, 95, or about 100 μM, where any number can be the upper or lower endpoint of a range. In still another aspect, the concentration of calcium ions in the inorganic component is about 10 μM or is about 100 μM. In one aspect, the calcium salt is calcium nitrate. In another aspect, the calcium salt is calcium chloride. In some aspects, both calcium nitrate and calcium chloride are used.

Magnesium Salts

In one aspect, the inorganic component includes one or more magnesium salts. In a further aspect, the one or more magnesium salts are selected from ammonium magnesium phosphate hydrate, magnesium bromide in an anhydrous or hexahydrate form, magnesium carbonate hydroxide pentahydrate, magnesium chloride in an anhydrous or hexahydrate form, magnesium fluoride, magnesium iodide, magnesium nitrate hexahydrate, dibasic magnesium phosphate, magnesium phosphate hydrate, magnesium sulfate in an anhydrous or monohydrate or heptahydrate form, and any combination thereof.

In one aspect, the magnesium salt is present in an amount sufficient to provide a concentration of from 1 to 10 mM of magnesium ions in the inorganic component prior to mixing with the organic component. In another aspect, the concentration of magnesium ions in the inorganic component is about 1, 2, 3, 4, 5, 6, 7, 8, 9, or about 10 mM, where any number can be the upper or lower endpoint of a range. In still another aspect, the concentration of magnesium ions in the inorganic component is about 2 mM or is about 10 mM. In one aspect, the magnesium salt is magnesium sulfate heptahydrate.

Ammonium Salts

In one aspect, the inorganic component includes one or more ammonium salts. In a further aspect, the one or more ammonium salts are selected from ammonium acetate, ammonium bromide, ammonium carbamate, ammonium carbonate, ammonium chloride, ammonium dihydrogen phosphate, ammonium fluoride, ammonium formate, ammonium hydrogen difluoride, ammonium hydrogenoxalate hydrate, ammonium hydrogen sulfate, ammonium iodide, ammonium molybdate, ammonium nitrate, ammonium oxalate monohydrate, dibasic ammonium sodium phosphate tetrahydrate, ammonium sulfate, and combinations thereof.

In one aspect, the ammonium salt is present in an amount sufficient to provide a concentration of from 5 to 75 mM of ammonium ions in the inorganic component prior to mixing with the organic component. In another aspect, the concentration of ammonium ions in the inorganic component is about 5, 10, 15, 20, 25, 30, 35, 40, 45, 50, 55, 60, 65, 70, or about 75 mM, where any number can be the upper or lower endpoint of a range. In still another aspect, the concentration of ammonium ions in the inorganic component is about 10 mM or is about 50 mM. In one aspect, the ammonium salt is ammonium sulfate.

Manganese Salts

In one aspect, the inorganic component includes one or more manganese salts. In a further aspect, the one or more manganese salts are manganese (II) or manganese (III) salts. In still another aspect, the one or more manganese salts are selected from manganese (II) bromide in an anhydrous or tetrahydrate form, manganese (II) carbonate in an anhydrous or hydrate form, manganese (II) chloride in an anhydrous or hydrate or tetrahydrate form, manganese (II) fluoride, manganese (III) fluoride, manganese (II) formate hydrate, manganese (II) iodide, manganese (II) nitrate hydrate, manganese (II) sulfate in a hydrate or monohydrate form, and combinations thereof.

In one aspect, the manganese salt is present in an amount sufficient to provide a concentration of from 50 to 125 μM of manganese ions in the inorganic component prior to mixing with the organic component. In another aspect, the concentration of manganese ions in the inorganic component is about 50, 55, 60, 65, 70, 75, 80, 85, 90, 95, 100, 105, 110, 115, 120, or 125 μM, where any number can be the upper or lower endpoint of a range. In still another aspect, the concentration of manganese ions in the inorganic component is about 50 μM to 100 μM. In one aspect, the manganese salt is manganese (II) sulfate monohydrate.

Molybdenum Salts

In one aspect, the inorganic component includes one or more molybdenum salts. In a further aspect, the one or more molybdenum salts are selected from molybdenum (III) chloride, molybdenum (V) chloride, molybdenum (VI) dichloride dioxide, and combinations thereof. In an alternative aspect, the one or more molybdenum salts are molybdate salts such as sodium molybdate monohydrate or other molybdate salts discussed herein.

In one aspect, the molybdenum salt is present in an amount sufficient to provide a concentration of from 100 to 300 nM of molybdate ions in the inorganic component prior to mixing with the organic component. In another aspect, the concentration of molybdate ions in the inorganic component is about 100, 125, 150, 175, 200, 225, 250, 275, or 300 nM, where any number can be the upper or lower endpoint of a range. In still another aspect, the concentration of molybdate ions in the inorganic component is about 200 nM to 250 nM. In one aspect, the molybdenum salt is sodium molybdate monohydrate.

Nickel Salts

In one aspect, the inorganic component includes one or more nickel salts. In a further aspect, the one or more nickel salts are nickel (II) salts. In a still further aspect, the one or more nickel salts are selected from ammonium nickel (II) sulfate hexahydrate, nickel (II) acetate tetrahydrate, nickel (II) bromide in an anhydrous or hydrate or trihydrate form, nickel (II) carbonate, nickel (II) carbonate hydroxide tetrahydrate, nickel (II) chloride in a hexahydrate or hydrate or anhydrous form, nickel (II) fluoride, nickel (II) hydroxide, nickel (II) iodide, nickel (II) nitrate hexahydrate, nickel (II) sulfate in an anhydrous or heptahydrate form, and combinations thereof.

Zinc Salts

In one aspect, the inorganic component includes one or more zinc salts. In a further aspect, the one or more zinc salts are selected from zinc bromide in an anhydrous or dihydrate form, zinc chloride, zinc citrate dihydrate, zinc fluoride, zinc iodide, zinc molybdate, zinc nitrate hydrate, zinc phosphate, zinc sulfate heptahydrate, and combinations thereof.

In one aspect, the zinc salt is present in an amount sufficient to provide a concentration of from 0.1 to 5 mM of zinc ions in the inorganic component prior to mixing with the organic component. In another aspect, the concentration of zinc ions in the inorganic component is about 0.1, 0.5, 1, 1.5, 2, 2.5, 3, 3.5, 4, 4.5, or about 5 mM, where any number can be the upper or lower endpoint of a range. In still another aspect, the concentration of zinc ions in the inorganic component is about 1.7 mM. In one aspect, the zinc salt is zinc sulfate heptahydrate.

Copper Salts

In another aspect, the inorganic component includes one or more copper salts. In a further aspect, the one or more copper salts are copper (I) or copper (II) salts. In a still further aspect, the one or more copper salts are selected from copper (I) bromide, copper (I) chloride, copper (II) chloride in an anhydrous or dihydrate form, copper (II) fluoride in an anhydrous or hydrate form, copper (II) hydroxide, copper (II) iodide, copper (II) nitrate in a hemipentahydrate or hydrate form, copper (II) pyrophosphate, copper (II) sulfate in an anhydrous or pentahydrate form, and combinations thereof.

In one aspect, the copper salt is present in an amount sufficient to provide a concentration of from 10 to about 500 nM of copper ions in the inorganic component prior to mixing with the organic component. In another aspect, the concentration of copper ions in the inorganic component is about 10, 50, 100, 150, 200, 250, 300, 350, 400, 450, or about 500 nM, where any number can be the upper or lower endpoint of a range. In still another aspect, the concentration of copper ions in the inorganic component is about 150 nM to 250 nM. In one aspect, the copper salt is copper sulfate pentahydrate.

Cobalt Salts

In yet another aspect, the inorganic component includes one or more cobalt salts. In a further aspect, the one or more cobalt salts are cobalt (II) or cobalt (III) salts. In a still further aspect, the one or more cobalt salts are selected from ammonium cobalt (II) sulfate hexahydrate, cobalt (II) bromide, cobalt (II) carbonate, cobalt (II) chloride in an anhydrous or hexahydrate or hydrate form, cobalt (II) fluoride in an anhydrous or tetrahydrate form, cobalt (III) fluoride, cobalt (II) hydroxide, cobalt (II) iodide, cobalt (II) nitrate, cobalt (II) sulfate in a heptahydrate or hydrate form, and combinations thereof.

In one aspect, the cobalt salt is present in an amount sufficient to provide a concentration of from 0.5 to about 5 mM of cobalt ions in the inorganic component prior to mixing with the organic component. In another aspect, the concentration of cobalt ions in the inorganic component is about 0.5, 1, 1.5, 2, 2.5, 3, 3.5, 4, or about 5 mM, where any number can be the upper or lower endpoint of a range. In still another aspect, the concentration of cobalt ions in the inorganic component is about 1 mM to 3 mM. In one aspect, the copper salt is cobalt (II) chloride hexahydrate.

Additional Components

In another aspect, the inorganic component can include additional inorganic or metal salts not already listed including but not limited to, sodium salts such as sodium chloride, boric acid or borate salts, and other inorganic salts compatible with the culture of microorganisms.

The inorganic component of the culture medium can be prepared by adding one or more salts to water at a desired concentration. If more than one salt is used, the salts can be added sequentially to water or one at a time. The pH of the inorganic component can be adjusted. In one aspect, the pH of the inorganic component can be less than or equal to 3, or less than or equal to 2. In another aspect, the pH of the inorganic component can be 1, 1.5, 2, 2.5, or 3, where any value can be a lower and upper endpoint of a range.

In one aspect, the inorganic component includes potassium ions at a concentration of from 1 to 25 mM, ammonium ions at a concentration of from 5 to 75 mM, magnesium ions at a concentration of from 1 to 10 mM, and calcium ions at a concentration of from 10 to 100 μM.

IV. Carbo-Ionic Cultures and Extracts

A satisfactory microbiological culture contains available sources of hydrogen donors and acceptors, carbon, nitrogen, sulfur, phosphorus, inorganic salts and, in certain cases, vitamins or other growth-promoting substances. For example, the addition of peptone provides a readily-available source of nitrogen and carbon. Furthermore, the use of different types of media results in different growth rates and different stationary phase densities. A rich media results in a short doubling time and higher cell density at stationary phase. Minimal media results in slow growth and low final cell densities. Efficient agitation and aeration increase final cell densities.

The microorganisms described herein are cultured or fermented in a culture medium composed of the organic and inorganic components as described above. In one aspect, prior to culturing, the organic and inorganic components are prepared independently and subsequently mixed to produce the culture medium. Depending upon the compounds and concentration thereof present in the organic and inorganic components, the volume of the organic and inorganic components present in the culture medium can vary. In one aspect, the volume ratio of organic component to inorganic component is from 5:1 to 1:5. In another aspect, the volume ratio of organic component to inorganic component is from 5:1, 4:1, 3:1, 2:1, 1.5:1, 1:1, 1:1.5, 1:2, 1:3, 1:4, or 1:5, where any ratio can be a lower and upper endpoint of a range (e.g., 2:1 to 1:2, 1:1.5 to 1.5:1).

In one aspect, the culture medium includes:

(a) an organic component comprising water, a meat extract in the amount of from 0.1 to 5 g/L, a yeast extract in the amount of 0.1 to 5 g/L, a peptone in the amount of from 0.1 to 10 g/L, and a salt in the amount of from 0.1 to 10 g/L; and (b) an inorganic component comprising water, potassium ions at a concentration of from 1 to 25 mM, ammonium ions at a concentration of from 5 to 75 mM, magnesium ions at a concentration of from 1 to 10 mM, and calcium ions at a concentration of from 10 to 100 μM, wherein the volume ratio of organic component to inorganic component is from 5:1 to 1:5, from 2:1 to 1:2, or from 1.5:1 to 1:1.5.

Culturing or fermenting of host cells can be accomplished by any technique known in the art. In one aspect, batch fermentation can be conducted. In batch fermentation, the composition of the culture medium is set at the beginning and the system is closed to future alterations. In some aspects, a limited form of batch fermentation may be carried out, wherein factors such as oxygen concentration and pH are manipulated, but additional carbon is not added. Continuous fermentation methods are also contemplated. In continuous fermentation, equal amounts of a defined medium are continuously added to and removed from a bioreactor. In other aspects, microbial cells are immobilized on a substrate. Fermentation may be carried out on any scale and may include methods in which literal "fermentation" is carried out as well as other culture methods that are non-fermentative.

In one aspect, the microorganisms can be cultured for a period of from 2 days to 2 weeks, or for about 2, 3, 4, 5, 6, 7, 8, 9, 10, 11, 12, 13, or 14 days, where any value can be the lower or upper endpoint of a range. In one aspect, the microorganisms are cultured for 10 days.

In another aspect, the microorganisms can be cultured at any temperature appropriate for the microorganisms, with the understanding that the temperature may vary according to the microorganism (for example, a thermophilic microorganism may require a higher culture temperature than a mesophile). In one aspect, the microorganisms are cultured at a temperature of from 20 to 37° C., or are cultured at about 20, 21, 22, 23, 24, 25, 26, 27, 28, 29, 30, 31, 32, 33, 34, 35, 36, or 37° C., where any value can be the lower or upper endpoint of a range. In one aspect, when the microorganisms are *A. ferrooxidans*, they can be cultured at about 26° C.

In certain aspects, after culturing the microorganisms for a sufficient time, the microbial cells can be lysed with one or more enzymes. For example, when the microbial cells are fungal, the fungal cells can be lysed with lyticase. In one aspect, the lyticase concentration can be 500, 600, 700, 800, 900, or 1000 μL per liter of culture, where any value can be the lower or upper endpoint of a range.

In addition to or in place of enzymes, other components can be used to facilitate lysis of the microbial cells. In one aspect, chitosan can be used in combination with an enzyme to lyse the microbial cells. Chitosan is generally composed of glucosamine units and N-acetylglucosamine units and can be chemically or enzymatically extracted from chitin, which is a component of arthropod exoskeletons and fungal and microbial cell walls. In certain aspects, the chitosan can be acetylated to a specific degree of acetylation. In one aspect, the chitosan is from about 60% to about 100% acetylated, 70% to 90%, 75 to 85%, or about 80% acetylated. The molecular weight of the chitosan can vary, as well. For example, the chitosan can comprise about 3, 4, 5, 6, 7, 8, 9, 10, 11, 12, 13, 14, 15. 16, 17, 18, 19, or 20 glucosamine units and/or N-acetylglucosamine units. In another aspect, the chitosan includes 5 to 7 glucosamine units and/or N-acetylglucosamine units. In one aspect, chitosan can be added until a concentration of 0.0015, 0.0025, 0.005, 0.0075, 0.01, 0.015, 0.02, 0.03, 0.04, or 0.05% (where any value can be an upper or lower endpoint of a range) is achieved in the culture. Still further in this aspect, the chitosan is present at a concentration of 0.01%.

In one aspect, the microbial cultures are used without further processing in the applications that follow (i.e., with whole, growing/reproducing cells). In an alternative aspect, the cells are filtered out using a filter membrane such as, for example, filter with a 1-2 μm size cutoff. Further in this aspect, the filtrate is preserved and used as the microbial extract in the applications that follow. In still another aspect, the filtrate can be partially or fully dried to produce a solid or powder (such as, for example, by lyophilization) prior to use. Further in this aspect, the filtrate can be resuspended in water until it dissolves, with stirring and heating if necessary, or can be partially resuspended into a suspension or a slurry. In still another aspect, cells can be lysed as described previously and the composition including lysed cells can be used as the microbial extract in the applications that follow, either as-is or dried. In some aspects, the dried composition containing lysed cells can be reconstituted as a solution or slurry as described above for the filtrate. In still other aspects, the composition containing lysed cells can be further purified by filtration or another method prior to use as an extract and can be used as-is or dried and reconstituted as described above.

In one aspect, a dried filtrate, lysed cell culture, or whole cell culture can be reconstituted in water as a solution, suspension, or slurry and used in further applications. In another aspect, the filtrate, lysed cell culture, or whole cell culture can be used as-is, without further processing. In still another aspect, any of the solutions, suspensions, or slurries described above can be mixed together, with or without water or another solvent, and used in the applications that follow.

V. Carbo-Ionic Extracts as Power Sources

In one aspect, described herein are circuits containing the carbo-ionic extracts and compositions described herein. In another aspect, the circuits incorporate the extracts and compositions as electrolyte solutions, i.e., as in a battery. In a further aspect, the circuits include metal electrodes immersed in the extracts and compositions and wired to one another to provide for transfer of electric charge. In one aspect, the electrodes are made from zinc, cadmium, copper, silver, graphite, rhodium, or lead. In one aspect, the electrodes are copper and zinc. In a further aspect, the circuits are arranged as series or as parallel circuits.

In another aspect, described herein is a battery containing the extracts and compositions described herein. In one aspect, the battery uses the extracts and compositions as electrolytes and incorporates a circuit of the type previously described. In another aspect, the battery can be used to power a device or part of a device such as those described herein. In one aspect, the battery is sufficient power for the device and no external power supply is needed. In an alternative aspect, the battery acts as a supplement to another power source.

In a further aspect, the battery and/or circuit described herein use only environmentally safe, natural materials from the extracts and compositions as electrolytes and can be disposed of and/or recycled by the consumer. In a still further aspect, the battery or circuit does not contain toxic chemicals or heavy metals. In another aspect, the battery or circuit does not present a fire hazard. In yet another aspect, at the end of its useful life, the battery or circuit can be disassembled, and the electrolyte removed and used for another application described herein (e.g., enhancing the growth of plants or microorganisms).

In one aspect, the equations in Table 1 below can be useful in modeling, describing, and/or predicting the behavior of microbial circuits and electronic devices using those circuits constructed using the extracts and compositions described herein:

TABLE 1

Equations Useful for Circuits Incorporating Microbial Extracts

| Property | Formula | Variable Descriptions | Units |
|---|---|---|---|
| Biological Charge | $BQ = OIDC \times \{CR \times pH \times [C](IC_e - IC_c)EZ\}$ | CR: culture redox<br>pH: culture pH<br>[C]: cell concentration (cells/mL)<br>EZ: extract size<br>IC: iron concentration<br>OIDC: organic-inorganic dilution coefficient | $\frac{mv \times mg}{mL}$ |
| Electric Power | $P = V \times I$ | V: electric potential<br>I: electric current | watts (W) |
| Biolight Electric Power[a] | $W_{BL} = OIDC \times V \times I$ | V: electric potential<br>I: electric current<br>OIDC: organic-inorganic dilution coefficient | watts (W) |
| Microbial Electric Current | $I = OIDC \times P/V$ | V: electric potential<br>P: microbial electric power<br>OIDC: organic-inorganic dilution coefficient | amperes (A) |
| Photon Emission Duration[a] | $PED = (P \times BQ \times \lambda)$ | P: microbial electric power<br>BQ: biological charge<br>λ: color wavelength | $\frac{W \times mv \times mg}{mL}$ |

[a]Equations specific to circuits including an LED or other light-producing element.

VI. Applications of Carbo-Ionic Extracts

In one aspect, the compositions and extracts described herein are useful in a variety of applications such as, for example, powering lighting sources, powering warming and cooling devices, and powering battery operated or other electrical devices in a variety of environments and settings.

Lighting Applications

In one aspect, for any device or in any situation where lighting is required and where use of an LED is suitable, the compositions and extracts disclosed herein can be incorporated into a circuit as described previously, wherein the circuit can provide lighting for one or more of: cell phones, medical instruments, holiday lighting displays, handheld flashlights, indicator lights on radar or sonar equipment, digital displays of alphanumeric information, billboards, automobiles (both interior and exterior), airport runways, train tracks, subways, highways, street signs, traffic lights, auxiliary lighting for building safety, exit signs and other lighted signs, flares, night-vision equipment, telescopes, binoculars, rifle scopes, distance finders, and the like.

Warming and Cooling Applications

In another aspect, wherever a temperature differential is required, the compositions and extracts disclosed herein can be incorporated into a circuit as described previously, wherein the circuit can provide warming and/or cooling for one or more of: clothing including, but not limited to, gloves, hats, coats, shoes, socks, blankets, or baby clothing; climate control in buildings including, but not limited to, floor heating, roof heating, building heating, water heaters, fans, and the like; food preparation and storage including but not limited to, refrigerators, freezers, beverages coolers and warmers, food warmers, ice chests, cooking apparatuses including stoves and grills, and the like. In still another aspect, the compositions and extracts disclosed herein can be used as add-ins or backups to other power sources such as, for example, gas, coal, nuclear, solar, or wind energy, or can be used during power outages instead of or in addition to generators.

Battery-Powered and Electrical Devices

In one aspect, the compositions and methods described herein can be incorporated into a circuit as described previously, wherein the circuit can be incorporated into an electronic device such as a battery of any size including a rechargeable battery, a key fob or remote control, an electronic reading device, a laptop or portable computer, or similar. In another aspect, the circuit can be incorporated into a kitchen appliance such as, for example, a microwave, toaster, coffee maker, oven, electric knife, food and beverage slicers, grinders, mixers, and dispensers, blenders, and the like. In still another aspect, the circuit can be incorporated into a television, portable video device, radio, speaker, microphone, video game console or controller, headphones, sound canceling equipment, or similar. In still another aspect, the circuit can be incorporated into a toy, a bicycle or tricycle, a musical instrument, a prosthetic limb, pacemaker, a CPAP device, a device for stimulating muscle growth and regeneration, or an insulin pump or other powered medical implant, a thermometer, a hearing aid, eyeglasses, another medical device, a scientific instrument such as, for example, a microscope, a power tool such as an air compressor, a gas detection device, a smoke detector, or an electric toothbrush or other small personal hygiene or grooming device. In one aspect, the circuit can be used in the transportation industry, for example, in automobiles, trucks, trains, buses and other means of public transportation, subways, watercraft of various sizes, aircraft, drones, motorcycles, golf carts, and the like. In another aspect, the circuit can be used in any type of pump (i.e., water, sewage, oil field, marine, swimming pool or hot tub, artificial heart). In yet another aspect, the circuit can be incorporated into electric fencing egress and control, a clock or other timekeeping device, irrigation systems and landscaping equipment, a cash register, voting equipment, buzzers, security systems, pest control devices, and equipment for industrial or home cleaning and sterilizing.

In one aspect, the devices can be wireless devices. In an alternative aspect, the devices may optionally require wires for operation.

Environmental Suitability

Devices and applications of the compositions and extracts disclosed herein are suitable for use in a variety of environments. In one aspect, the devices can be used in applications under water, at high altitudes, at temperature extremes both high and low, in situations where traditional batteries and/or power sources would present a flammability hazard or explosion risk, in space, in laboratories and industrial facilities, in remote locations, and in areas with weather extremes including wind, rain, sandstorms, and the like.

VII. Methods for Enhancing the Growth of Microorganisms

In one aspect, the compositions and extracts disclosed herein can be used as a culture medium for commercially important microorganisms or can be used as a supplement to an existing medium. Further in this aspect, culturing microorganisms in the presence of the compositions and extracts disclosed herein can lead to enhanced growth rates and/or enhanced production of desirable metabolites.

In a further aspect, the compositions and extracts disclosed herein are useful in culturing the following types or organisms: (1) *Saccharomyces cerevisiae* for use in yeast doughs, brewing beer and wine, genetic research, and production of desirable secondary metabolites including the enzymes invertase and raffinase; *Kluyveromyces* species for the commercial production of lactase; and *Candida* species for the commercial production of lipase; (2) *Lactobacillus* species for use in making fermented foods such as yogurt, kefir, cheese, sauerkraut, pickles, hard cider, wine, and beer as well as for the commercial production of lactic acid and engineered *Lactobacillus* species engineered to produce protein drugs such as, for example, insulin; (3) *Pyrococcus furiosus, Thermus aquaticus, Bacillus stearothermophilus, Thermus filiformis, Thermus* thermophiles, and other thermophiles for production of heat stable polymerases for use in the polymerase chain reaction (PCR); (4) *Xanthomonas* species for production of xanthan gum, used in a variety of food and cosmetic products; (5) *Aspergillus niger*, used in the production of citric acid and fermentation of sake and other alcoholic beverages and this and other *Aspergillus* species for commercial production of α-amylase, aminoacylase, glucoamylase, catalase, glucose oxidase, lactase, pectinase, pectin lyase, and protease; *Trichoderma* species for the commercial production of cellulose; *Mucor miehei* for the commercial production of rennet; *Rhizopus* species for the commercial production of lipase; and *Mortierella* species for the commercial production of raffinase; (6) *Clostridium* species for production of botulinum toxin for cosmetic and medical purposes as well as the production of butanol (i.e., from *Clostridium acetobutylicum*); (7) *Streptomyces* species for production of antibiotics, antiparasitic, antineoplastic, and antifungal compounds including, but not limited to, chloramphenicol, daptomycin, fosfomycin, lincomycin, neomycin, nourseothricin, puromycin, streptomycin, tetracycline, oleandomycin, tunicamycin, mycangimycin, boromycin, bambermycin, clavulanic acid, guadinomine, ivermectin, migrastatin, bleomycin, erythromycin, geldanamycin, and the like; (8) *Penicillium* species for the production of penicillin and other beta-lactam antibiotics and precursors to semi-synthetic beta-lactam antibiotics; (9) *Acetobacter aceti* for production of acetic acid; (10) *Bacillus* species for commercial production of α-amylase, β-amylase, glucose isomerase, penicillin amidase, and protease; *E. coli* for commercial production of asparaginase; and *Klebsiella* species for commercial production of pullulanase; (11) *Trichoderma polysporum* for the production of cyclosporine A, (12) yeasts such as *Monascus purpureus* for the production of statin drugs for lowering blood cholesterol; (13) *Bacillus thuringiensis* for the production of insecticides, and other commercially important bacteria, fungi, algae, and cyanobateria.

In an alternative aspect, the compositions and extracts disclosed herein can be used as an animal food or animal supplement. Further in this aspect, the compositions and extracts disclosed herein may contain vitamins, minerals, proteins, peptides, carbohydrates, and/or other nutrients essential for animal growth and development and/or maintenance of animal health.

VIII. Methods for Enhancing the Physiological Properties of Plants

The compositions and extracts described herein can enhance the physiological properties of a plant. The term "physiological property" as defined herein includes any physical, chemical, or biological feature that is improved using the compositions and extracts described herein. In one aspect, the compositions and extracts can enhance the growth rate of the plant.

Herein, "plant" is used in a broad sense to include, for example, any species of woody, ornamental, crop, cereal, fruit, or vegetable plant, as well as photosynthetic green algae. "Plant" also refers to a plurality of plant cells that are differentiated into a structure that is present at any stage of the plant's development. Such structures include, but are not limited to, fruits, shoots, stems, leaves, flower petals, roots, tubers, corms, bulbs, seeds, gametes, cotyledons, hypocotyls, radicles, embryos, gametophytes, tumors, and the like. "Plant cell," "plant cells," or "plant tissue" as used herein refer to differentiated and undifferentiated tissues of plants including those present in any of the tissues described above, as well as to cells in culture such as, for example, single cells, protoplasts, embryos, calluses, etc.

The selection of the plant used in the methods described herein can vary depending on the application. For example, a specific plant can be selected that produces certain desirable metabolites. Current techniques for producing most plant metabolites are expensive. For example, large amounts of fresh plant biomass must be cultivated and harvested, and expensive and time-consuming extraction methods must be used. The compositions and extracts described herein enhance the production of metabolites from plants that naturally produce these metabolites.

In one aspect, plant cells when contacted with the compositions and extracts described herein exhibit enhanced production of various desirable metabolites. Recipient cell targets include, but are not limited to, meristem cells, Type I, Type II, and Type III callus, immature embryos and gametic cells such as microspores, pollen, sperm, and egg cells. It is contemplated that any cell from which a fertile plant may be regenerated is useful as a recipient cell. Type I, Type II, and Type III callus may be initiated from tissue sources including, but not limited to, immature embryos, immature inflorescences, seedling apical meristems, microspores, and the like. Those cells that are capable of proliferating as callus are also useful herein. Methods for growing plant cells are known in the art. In one aspect, plant calluses grown from 2 to 4 weeks can be used herein. The plant cells can also be derived from plants varying in age. For example, plants that are 80 days to 120 days old after pollination can be used to produce calluses useful herein.

The plant cells can be contacted with the compositions and extracts described herein in a number of different ways. In one aspect, the compositions and extracts described herein can be added to media containing the plant cells or can be the media containing the plant cells. In another aspect, the compositions and extracts can be injected into the plant cells via syringe. The amount of extract and the duration of exposure to the extract can vary as well.

Once the plant cells have been in contact with the compositions and extracts for a sufficient time to produce a desired metabolite, the metabolite is isolated. In one aspect, the metabolite is extracted from the media containing the plant cells. The selection of extraction solvent can vary depending on the solubility of the metabolite.

In other aspects, the compositions and extracts described herein can increase the growth rate of a plant. In particular, the compositions and extracts described herein are effective in accelerating plant development in the early stages of tissue culturing. By accelerating plant development in the early stages, it is possible to harvest more metabolites from the plant. Additionally, traditional methods for tissue culture involve the use of synthetic growth factors such as 2,4-dichlorophenoxyacetic acid (2,4-D), which can pose environmental concerns. The compounds and extracts described herein avoid the need for such compounds.

In certain aspects, any of the compositions and extracts described above can be used in combination with a polysaccharide to enhance one or more physiological properties of the plant. In one aspect, the plant cells are first contacted with the compositions and extracts, then subsequently contacted with the polysaccharide. In another aspect, the plant cells are first contacted with the polysaccharide, then subsequently contacted with the compositions or extracts. In a still further aspect, the plant cells are contacted simultaneously with the polysaccharide and the compositions and extracts.

In one aspect, the polysaccharide includes chitosan, glucosamine (GlcN), N-acetylglucosamine (NAG), or any combination thereof. Chitosan is generally composed of GlcN and NAG units and can be chemically or enzymatically extracted chitin, which is a component of arthropod exoskeletons and fungal and microbial cell walls. In certain aspects, the chitosan can be acetylated to a specific degree of acetylation in order to enhance tissue growth during culturing as well as metabolite production. In one aspect, chitosan isolated from shells of crab, shrimp, lobster, and/or krill is useful herein. In one aspect, the chitosan is in a solution of water and acetic acid at less than 1% by weight, less than 0.75% by weight, less than 0.5% by weight, less than 0.25% by weight, or less than 0.1% by weight. In another aspect, the amount of chitosan that is applied to the plant cells is from 0.1% to 0.01% by weight, from 0.075% to 0.025% by weight, or is about 0.05% by weight. The polysaccharides used herein are generally natural polymers and thus present no environmental concerns. Additionally, the polysaccharides can be used in acceptably low concentrations. In certain aspects, however, the polysaccharides can be used in combination with one or more plant growth regulators.

In one aspect, the plant growth regulator is an auxin, a cytokinin, a gibberellin, abscisic acid, or a polyamine. In a further aspect, the auxin is a natural or synthetic auxin. In a still further aspect, the auxin is indole-3-acetic acid (IAA), 4-chloroindole-3-acetic acid (4-Cl-IAA), 2-phenylacetic acid (PAA), indole-3-butyric acid (IBA), 2,3-dichlorophenoxyacetic acid (2,4-D), a-naphthalene acetic acid (α-NAA), 2-methoxy-3,6-dichlorobenzoic acid (dicamba), 4-amino-3,5,6-trichloropicolinic acid (torden or picloram), 2,4,5-trichloropicolinic acid (2,4,5-T), or a combination thereof. In another aspect, the cytokinin is zeatin, kinetin, 6-benzylaminopurine, diphenylurea, thidizuron (TDZ), 6-(γ,γ-dimethylallylamino)purine, or a combination thereof. In another aspect, the gibberellin is gibberellin A1 (GA1), gibberellic acid (GA3), ent-gibberellane, ent-kaurene, or a combination thereof. In yet another aspect, the polyamine is putrescine, spermidine, or a combination thereof.

In one aspect, the plant cell or callus is first contacted with a polysaccharide and subsequently contacted with a plant growth regulator. In another aspect, the plant cell or callus is first contacted with a plant growth regulator and subsequently contacted with a polysaccharide. In an alternative aspect, the plant cell or callus is simultaneously contacted with a polysaccharide and a plant growth regulator. In a further aspect, the plant cell or callus is only contacted with a polysaccharide and is not contacted with a plant growth regulator.

The plant cells can be contacted with the polysaccharide using a number of techniques. In one aspect, the plant cells or reproductive organs (e.g., a plant embryo) can be cultured in agar and medium with a solution of the polysaccharide. In other aspects, the polysaccharide can be applied to a plant callus by techniques such as, for example, coating the callus or injecting the polysaccharide into the callus. In this aspect, the age of callus can vary depending on the type of plant. The amount of polysaccharide can vary depending upon, among other things, the selection and number of plant cells. The use of the polysaccharide in the methods described herein permits rapid tissue culturing at room temperature. Due to the ability of the polysaccharide to prevent microbial contamination, the tissue can grow for extended periods of time ranging from days to several weeks. Moreover, tissue culturing with the polysaccharide can occur in the dark and/or light. As discussed above, the plant cells are also contacted with any of the compositions or extracts described above. Thus, the use of the polysaccharides and compositions and extracts described herein is a versatile way to culture and grow plant cells—and, ultimately, plants of interest—with enhanced physiological properties.

In other aspects, the plant cells can be cultured in a liquid medium on a larger scale in a bioreactor. For example, plant cells can be cultured in agar and medium, then subsequently contacted with the compositions and extracts described herein. After a sufficient culturing time (e.g., two to four weeks), the plant cells are introduced into a container with the same medium used above and, additionally, the polysaccharide. In certain aspects, the polysaccharide can be introduced with anionic polysaccharides including, but not limited to, alginates (e.g., sodium alginate, calcium alginate, potassium alginate, etc.). After the introduction of the polysaccharide, if using, the solution is mixed for a sufficient time to produce a desired result (e.g., production of a desired metabolite). Alternatively, the initial liquid medium in the bioreactor can include any of the compositions and/or extracts described herein.

In one aspect, provided herein is a plant grown by the process that involves contacting plant gamete cells or a plant reproductive organ with the compositions and extracts disclosed herein. In a further aspect, the plant is produced by the following method:

(a) contacting a plant callus with the compositions and extracts;

(b) culturing the plant callus; and (c) growing the plant from the plant callus.

In a further aspect, the same method can be applied to other plant parts including fruits, stems, roots, tubers, corms, bulbs, flowers, buds, seeds, and the like. In a still further aspect, the same method can be applied to an entire plant.

In one aspect, the plant callus is immersed in a solution of polysaccharide (e.g., chitosan), then inoculated with the compositions and/or extracts. In another aspect, the plant callus can be from 2 days up to 20 days old prior to inoculation with the compositions and/or extracts described herein. The plant callus is then allowed to grow until it is of sufficient weight and size. In one aspect, the plant callus is allowed to grow (i.e., culture) for 1 to 10 weeks after inoculation. Following growth or culture of the callus for a sufficient period of time, desired metabolites can be collected according to methods known in the art; said methods are specific to the desired metabolites and make use of properties ranging from molecular size to charge to hydrophobicity or hydrophilicity to other properties useful for collection and purification of the metabolites.

VIII. Anti-UV Applications

The carbo-ionic extracts produced herein may be applied to any material that may benefit from a reduction in UV radiation. The exact formulation of the extract plus any carriers can be adjusted based on the desired use. In one aspect, the extract is formulated with only non-toxic components if it is to be used on a human or animal or with another microorganism, such as in a fermentation process or on an agricultural product. In another aspect, the extract can be mixed with other substances to provide UV-protective properties to the overall composition. In still another aspect, if coated on the material to be protected, the extract itself can be covered with a further protective coating to project, for example, against mechanical wear and damage.

In the case when the extract is applied to the surface of an article, it can be applied using techniques known in the art such spraying or coating. In other aspects, the extract can be intimately mixed with a substance or material that ultimately produces the article. For example, the extract can be mixed with molten glass so that the extract is dispersed throughout the final glass product.

In one aspect, the extract is formulated or applied in such a manner as to block approximately 50%, 60%, 70%, 80%, 90%, 95%, or 99% of the UV radiation that encounters the extract, where any value can be a lower and upper end-point of a range (e.g., 60% to 95%). In a further aspect, the extract can also be formulated to block these percentages of particular UV wavelengths, or, more generally, to block these percentages of UVA, UVB, or UVC radiation.

Extracts according to the present disclosure can be used for a variety of purposes. These purposes include, but are not limited to, the following:

1. blocking UV radiation or other types of radiation;
2. protecting human skin against damage and/or skin cancer induced by UV radiation or other types of radiation;
3. protecting against side effects of radiation used in cancer treatments;
4. protecting animals from deleterious effects of UV radiation or other radiation;
5. protecting plastic, fiberglass, glass, rubber, or other solid surfaces from UV radiation or other radiation;
6. providing a UV radiation screen or screen for other types of radiation;
7. protecting astronauts and/or other persons or organisms as well as equipment during space trips;
8. enhancement of industrial fermentation processes or other processes requiring energy by allowing the use of UV radiation in connection with the process to supply additional energy and thus to increase the ultimate energy-requiring output of the cells without substantially killing the fermenting organism;
9. protection of experimentation, fermentation, biochemical, and/or biological processes under the presence of UV radiation, for example in extraterrestrial conditions such as on the moon or Mars; and
10. protection of agricultural plants, particularly agricultural plants in which the revenue-producing part of the plant is above ground, such as fruits, vine vegetables, beans and peas, and leaf vegetables.

In one aspect, the carbo-ionic can be applied to an agricultural plant. In one aspect, the plant can be one that produces fruit or vegetable, such as, for example, a watermelon or a tomato. Further in this aspect, the extract can be applied during at least a part of the plant's growth to increase the amounts of one or more nutrients of the fruit or vegetable, such as a vitamin, mineral, or other recommended dietary component. In one specific aspect, the amount of lycopene can be increased (which may be accompanied by a decrease in carotene or other less-valuable nutrients formed by competing pathways). In another aspect, the amount of a flavor-enhancing component, such as glucose, can be increased. Further in this aspect, an increase in glucose can help protect against water loss.

In one aspect, the carbo-ionic extract can be applied for about 25%, 50%, 75%, 90%, 95%, or 99% of the fruit or vegetable's on-plant life, where the on-plant life includes the time span from the formation of a separate body that will constitute the fruit or vegetable (in some aspects, excepting flowers) until the fruit or vegetable is harvested. In one aspect, the extract can be first applied when the fruit or vegetable is sufficiently large to no longer be substantially protected from UV radiation by leaves. In another aspect, the extract can first be applied five days, one week, or two weeks prior to harvest. Further in this aspect, application at this later stage can be particularly useful with fruits or vegetables in which an increase in a nutrient or flavor-enhancing component can be obtained by protecting the fruit or vegetable from UV radiation later in its on-plant life.

In one aspect, the carbo-ionic extract can be applied once or multiple times to each fruit or vegetable. In another aspect, it can be applied weekly, or it can be reapplied after the fruit or vegetable is exposed to rain or after a turning process. In another aspect, the agricultural plant can be another food crop that grows above ground and is exposed to natural UV radiation, wherein the agricultural product produced can be a fruit, leaf, seed, flower, grain, nut, stem, vegetable, or mushroom.

In another aspect, it is desirable for agricultural plants that do not produce parts typically consumed by humans to be protected from UV irradiation. In a further aspect, these other agricultural plants can includes sources of fibers such as, for example, cotton and linen (flax), of cork, of wood or lumber, of feedstocks for producing ethanol or biodiesel (including, but not limited to, sugar beet, sugarcane, cassava, sorghum, corn, wheat, oil palm, coconut, rapeseed, peanut, sunflower, soybean, and the like), of animal feedstocks or fodder, or of decorative or horticultural plants.

In one aspect, any part of the plant can be coated with the carbo-ionic extract, including, but not limited to, the part of the plant that is collected during harvest. In an alternative aspect, the harvested part of the plant is not coated, but another part can be coated with the extracts disclosed herein. In addition to the aspects already described, in one aspect, coating a plant with the extracts described herein can prolong the life of the plant, increase production capacity of a desired product, can increase the growth rate of the plant relative to an untreated plant of the same type, can increase production of a desired metabolite that might otherwise decrease due to UV-induced stress, can increase yield of a crop of such plants, and the like.

In a further aspect, application can be accomplished with a commercial sprayer. In another aspect, application can be only on the upper portions of the fruit or vegetable, which are exposed to substantially greater amounts of UV radiation than the lower portions of the fruit or vegetable.

In another aspect, provided herein is a pharmaceutical composition containing the carbo-ionic extracts described herein. In one aspect, the pharmaceutical composition can be applied to a subject, wherein the subject is exposed to radiation. In one aspect, the radiation is applied as a strategy to treat cancer. In another aspect, the pharmaceutical composition is used to prevent radiation-induced cellular and DNA damage. In another aspect, dosage ranges of the extract in the pharmaceutical composition can vary from 0.01 g extract/mL of pharmaceutical composition to 1 g extract/mL of pharmaceutical composition, or can be 0.01, 0.02, 0.025, 0.05, 0.075, or 1 g extract/mL of pharmaceutical composition. In an alternative aspect, provided herein is a cosmetic composition containing the carbo-ionic extracts produced herein. Further in this aspect, the cosmetic composition can be a cleanser, lotion, cream, shampoo, hair treatment, makeup, lip treatment, nail treatment, or related composition. In still a further aspect, the compositions containing the extracts can have both pharmaceutical and cosmetic applications. In yet another aspect, the compositions containing the extracts can be used in veterinary medicine.

The cosmetic compositions can be formulated in any physiologically acceptable medium typically used to formulate topical compositions. The cosmetic compositions can be in any galenic form conventionally used for a topical application such as, for example, in the form of dispersions of aqueous gel or lotion type, emulsions of liquid or semi-liquid consistency of the milk type, obtained by dispersing a fatty phase in an aqueous phase (O/W) or vice versa (W/O), or suspensions or emulsions of soft, semi-solid or solid consistency of the cream or gel type, or alternatively multiple emulsions (W/O/VV or O/W/O), microemulsions, vesicular dispersions of ionic and/or non-ionic type, or wax/aqueous phase dispersions. These compositions are prepared according to the usual methods.

The cosmetic compositions can also contain one or more additives commonly used in the cosmetics field, such as emulsifiers, preservatives, sequestering agents, fragrances, thickeners, oils, waxes or film-forming polymers. In one aspect, in any of the above scenarios, the pharmaceutical, cosmetic, or veterinary composition also includes additional UV-protective compounds or UV-blocking agents such as, for example, zinc oxide, titanium dioxide, carotenoids, oxybenzone, octinoxate, homosalate, octisalate, octocrylene, avobenzone, or a combination thereof.

In one aspect, the composition is a sunscreen. A sunscreen can be formulated with any of the extracts produced herein. In addition to the extract, the sunscreen in certain aspects can be formulated with one or more UV-protective compounds or UV-blocking agents listed above. The sunscreen can be formulated as a paste, lotion, cream, aerosol, or other suitable formulations for topical use. In certain aspects, the sunscreen can be formulated as a transparent composition.

In one aspect, the cosmetic composition can be a film composed of the carbo-ionic extracts produced herein that can be directly applied to the skin. For example, the film can be composed of a biocompatible material such as a protein or oligonucleotide, where the extract is coated on one or more surfaces of the film or, in the alternative dispersed throughout the film. For example, the film can be composed of DNA. In this application, the films can be used as a wound covering and provide protection from UV photodamage. The films can also be prepared so that they are optically transparent. Here, it is possible to view the wound without removing the covering and exposing the wound. The films can also include other components useful in cosmetic applications such as, for example, compounds to prevent or reduce wrinkles.

In one aspect, the pharmaceutical, cosmetic, or veterinary compositions described herein are applied to subjects. In one aspect, the subject is a human, another mammal, or a bird. In a further aspect, the mammal is a pet such as a dog or cat or is livestock such as horses, goats, cattle, sheep, and the like. In an alternative aspect, the bird is a pet bird or is poultry such as, for example, a chicken or turkey. In any of these aspects, the compositions can be applied to skin, fur, feathers, wool, hooves, horns, or hair as appropriate and applicable.

In another aspect, provided herein is a paint, dye, stain, or ink containing the carbo-ionic extracts disclosed herein. In one aspect, there are several benefits to having a paint that is resistant to UV irradiation. In a further aspect, imparting UV resistance to a paint slows or stops photodegradation, bleaching, or color fading. In another aspect, a paint with UV resistance prevents chemical modification of exposed paint surfaces. Further in this aspect, chemical modification of exposed paint surfaces includes change in finish, structural changes in binders, flaking, chipping, and the like. In one aspect, the paint provided herein resists these changes.

In still another aspect, provided herein is an article coated with the carbo-ionic extracts disclosed herein. In one aspect, the article is made of glass, plastic, metal, wood, fabric, or any combination thereof. In one aspect, the article is a construction material such as, for example, steel, concrete or cement, brick, wood, window or door glass, fiberglass, siding, wallboard, a flooring material, masonry, mortar, grout, stone, artificial stone, stucco, shingles, roofing materials, and the like. In an alternative aspect, the material is an aeronautical or aerospace material such as, for example, the metal or metal alloy body of an aircraft or spacecraft, paint on the body of an aircraft or spacecraft, glass windows on an aircraft or spacecraft, carbon fiber composite, titanium or aluminum, a ceramic heat absorbing tile, and the like. In still another aspect, the article is a fabric article such as, for example, clothing, drapes, outdoor upholstery, a tent or outdoor pavilion, a flag or banner, or the like. In another aspect, the extract can be applied to the article to fine artwork, solid pieces (e.g., vases), and historical documents in order to preserve them. In another aspect, the extract can be applied to outdoor signs such as highway billboards and advertising.

In other aspects, the carbo-ionic extract can be incorporated within or throughout the article. In one aspect, the extract can be mixed with molten glass to produce glass article that are UV resistant such as, for example, sunglasses, car windshields, window glass, and eyeglasses. In another aspect, the glass article can be a bottle for storing a beverage or food container in order to increase the shelf-life of the beverage or food. It is contemplated that the extract can be applied externally to the glass articles as well.

In another aspect, the carbo-ionic extract can be mixed with fiberglass or plastics in order to reduce negative effects to aircraft, watercraft, boats, jet skis, decking, house siding, motor homes, sunroofs, and moon roofs that are constantly exposed to UV radiation. It is contemplated that the extract can be applied externally to the fiberglass or plastic articles as well.

In another aspect, the carbo-ionic extract can be mixed with rubber, silicon, or latex used to make a variety of articles such as water hoses, tires, and the like. It is contemplated that the extract can be applied externally to the rubber, silicone, or latex articles as well.

In another aspect, the carbo-ionic extract can be mixed with foams used to make a variety of articles such as automotive dashboard padding, seat cushions, and the like. It is contemplated that the extract can be applied externally to the foam articles as well.

In another aspect, the carbo-ionic extracts described herein can be incorporated into an optical film. In one aspect, the extract is applied to at least one surface of the film. In another aspect, the extract can be dispersed throughout the film. The film can be transparent, translucent or opaque. The film can be composed of, but not limited to, polyolefin resin, such as polyethylene (PE) or polypropylene (PP); polyester resin, such as polyethylene terephthalate (PET); polyacrylate resin, such as polymethyl (meth)acrylate (PMMA); polycarbonate resin; polyurethane resin or a mixture thereof. The optical film can be applied to any substrate where it is desirable to reduce or prevent UV exposure or damage. For example, the optical film can be applied to windows to reduce or prevent UV radiation from entering a structure (e.g., building, vehicle, etc.).

In another aspect, provided herein is a method of reducing or preventing the exposure of an item to UV radiation by applying the carbo-ionic extracts described herein to the item or incorporating the extract within/throughout the article. Further in this aspect, "reducing" is defined relative to an untreated control. That is, if two like items are exposed to equal amounts of UV radiation for an equal amount of time, but one has been treated with the UV-resistant extracts and the other has not, and some objective response is measured (e.g., color fading, structural degradation, plant size or yield, etc.), the treated item will appear to have been exposed to a lower amount of UV (for example, the color of the treated item will have faded less and will remain closer to the original, or a treated plant will appear larger and more vigorous and will have a greater yield, etc.). In some aspects, treatment with the extracts disclosed herein will prevent UV exposure from occurring. As used herein, "prevent" indicates that a treated item will not be affected, changed, or altered by UV exposure.

In one aspect, the carbo-ionic extract blocks from 50% to 100% of UV radiation from contacting the item. Further in this aspect, the extract blocks at least 50%, 55%, 60%, 65%, 70%, 75%, 80%, 85%, 90%, 95%, 99%, or 100% of UV radiation from contacting the item. In another aspect, the extract blocks from 50% to 100% of longwave UV radiation from contacting the item. Further in this aspect, the extract blocks at least 50%, 55%, 60%, 65%, 70%, 75%, 80%, 85%, 90%, 95%, 99%, or 100% of longwave UV radiation from contacting the item. In one aspect, the extract blocks from 50% to 100% of shortwave UV radiation from contacting the item. Further in this aspect, the extract blocks at least 50%, 55%, 60%, 65%, 70%, 75%, 80%, 85%, 90%, 95%, 99%, or 100% of shortwave UV radiation from contacting the item.

Depending upon the application, the carbo-ionic extract can prevent or reduce damage cause by UV radiation from limited to extended periods of time. By varying the amount of extract that is applied as well as the number of times the extract is applied, the degree of UV protection can be varied. In certain aspects, it may be desirable for the article to be protected from UV damage for a short period of time then subsequently biodegrade.

In another aspect, the carbo-ionic extracts produced herein can be used to reduce or prevent the growth of barnacles on boats and other water vehicles. In one aspect, the extract can be admixed with a paint that is typically applied to water vehicles, where the paint also includes chitosan. In one aspect, the chitosan can be acetylated to a specific degree of acetylation in order to enhance tissue growth during culturing as well as metabolite production. In one aspect, the chitosan is from 60% to about 100%, 70% to 90%, 75% to 85%, or about 80% acetylated. In one aspect, chitosan isolated from the shells of crab, shrimp, lobster, and/or krill is useful herein. The molecular weight of the chitosan can vary, as well. For example, the chitosan comprises about 3, 4, 5, 6, 7, 8, 9, 10, 11, 12, 13, 14, 15, 16, 17, 18, 19, or 20 glucosamine units and/or N-acetylglucosamine units. In another aspect, the chitosan includes 5 to 7 glucosamine units and/or N-acetylglucosamine units.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperatures, etc.) but some errors and deviations should be accounted for. Unless indicated otherwise, parts are parts by weight, temperature is in ° C. or is at ambient temperature, and pressure is at or near atmospheric. Numerous variations and combinations of reaction conditions (e.g. component concentrations, desired solvents, solvent mixtures, temperatures, pressures, and other reaction ranges and conditions) can be used to optimize the product purity and yield obtained from the described process. Only reasonable and routine experimentation will be required to optimize such processes and conditions.

Culture Media

Experiments were run in parallel with different proportions of ingredients in the cell culture media to determine optimum conditions for the development of devices. The nutrient broth used to produce the organic component is a powder produced by Scharlab (product no. 02-140-500) mixed with water. The nutrient broth is composed of meat extract (1 g/L), yeast extract (1 g/L), peptone (5 g/L), and sodium chloride (5 g/L).

Example media compositions are provided in Tables 2 through 7. In each instance, Solution 1 (organic component) and Solution 2 (inorganic component) are aseptically combined after separate preparation.

TABLE 2

| Original Culture Medium (9K Medium) |
| --- |
| Solution 1 |
| 0.8 g $(NH_4)_2SO_4$ |
| 0.4 g $K_2HPO_4$ |
| 2 g $MgSO_4 \cdot 7H_2O$ |
| 5.0 mL Wolfe's mineral solution[a] |
| 0.0025 g $Ca(NO_3)_2$ |
| 800 mL deionized $H_2O$ |
| Adjust solution to pH 2.3 with $H_2SO_4$ and filter sterilize |
| Solution 2 |
| 20 g $FeSO_4 \cdot 7H_2O$ |
| 200 mL deionized water |

[a]Wolfe's mineral solution: 1.5 g nitrilotriacetic acid, 3 g $MgSO_4 \cdot 7H_2O$, 0.5 g $MnSO_4 \cdot H_2O$, 1 g NaCl, 0.1 g $FeSO_4 \cdot 7H_2O$, 0.1 g $CoCl_2 \cdot 6H_2O$, 0.1 g $CaCl_2$, 0.1 g $ZnSO_4 \cdot 7H_2O$, 0.01 g $CuSO_4 \cdot 5H_2O$, 0.01 g $AlK(SO_4)_2 \cdot 12H_2O$, 0.3 g $H_3BO_3$, 0.01 g $Na_2MoO_4 \cdot H_2O$ in 1 L deionized water.

TABLE 3

| Adjusted 50/50 Medium |
|---|
| Organic |
| 6.5 g nutrient broth |
| 500 mL deionized $H_2O$ |
| Autoclave at 120° C. for 15 min |
| Solution 1 |
| 1.5 g $(NH_4)_2SO_4$ |
| 0.25 g $K_2HPO_4$ |
| 0.25 g $MgSO_4$•$7H_2O$ |
| 0.05 g KCl |
| 0.005 g $Ca(NO_3)_2$ |
| 350 mL deionized $H_2O$ |
| Adjust solution to pH 2.0 and autoclave at 120° C. for 15 min |
| Solution 2 |
| 22.11 g $FeSO_4$•$7H_2O$ |
| 150 mL deionized water |
| Adjust solution to pH 1.8 with $H_2SO_4$ and filter sterilize |

TABLE 4

| Adjusted 60/40 Medium |
|---|
| Organic |
| 7.8 g nutrient broth |
| 600 mL deionized $H_2O$ |
| Autoclave at 120° C. for 15 min |
| Solution 1 |
| 1.2 g $(NH_4)_2SO_4$ |
| 0.2 g $K_2HPO_4$ |
| 0.2 g $MgSO_4$•$7H_2O$ |
| 0.04 g KCl |
| 0.004 g $Ca(NO_3)_2$ |
| 280 mL deionized $H_2O$ |
| Adjust solution to pH 2.0 and autoclave at 120° C. for 15 min |
| Solution 2 |
| 17.69 g $FeSO_4$•$7H_2O$ |
| 120 mL deionized water |
| Adjust solution to pH 1.8 with $H_2SO_4$ and filter sterilize |

TABLE 5

| Modified 9K Medium |
|---|
| Solution 1 |
| 3.0 g $(NH_4)_2SO_4$ |
| 0.5 g $K_2HPO_4$ |
| 0.5 g $MgSO_4$•$7H_2O$ |
| 0.1 g KCl |
| 0.01 g $Ca(NO_3)_2$ |
| 700 mL deionized $H_2O$ |
| Adjust solution to pH 2.0 and autoclave at 120° C. for 15 min |
| Solution 2 |
| 44.22 g $FeSO_4$•$7H_2O$ |
| 300 mL deionized water |
| Adjust solution to pH 1.8 with $H_2SO_4$ and filter sterilize |

TABLE 6

| Adjusted 70/30 Medium |
|---|
| Organic |
| 9.1 g nutrient broth |
| 700 mL deionized $H_2O$ |
| Autoclave at 120° C. for 15 min |
| Solution 1 |
| 0.9 g $(NH_4)_2SO_4$ |
| 0.15 g $K_2HPO_4$ |
| 0.15 g $MgSO_4$•$7H_2O$ |
| 0.03 g KCl |
| 0.003 g $Ca(NO_3)_2$ |
| 210 mL deionized $H_2O$ |
| Adjust solution to pH 2.0 and autoclave at 120° C. for 15 min |
| Solution 2 |
| 13.266 g $FeSO_4$•$7H_2O$ |
| 90 mL deionized water |
| Adjust solution to pH 1.8 with $H_2SO_4$ and filter sterilize |

TABLE 7

| Adjusted 75/25 Medium |
|---|
| Organic |
| 9.75 g nutrient broth |
| 750 mL deionized $H_2O$ |
| Autoclave at 120° C. for 15 min |
| Solution 1 |
| 0.75 g $(NH_4)_2SO_4$ |
| 0.125 g $K_2HPO_4$ |
| 0.125 g $MgSO_4$•$7H_2O$ |
| 0.025 g KCl |
| 0.0025 g $Ca(NO_3)_2$ |
| 170 mL deionized $H_2O$ |
| Adjust solution to pH 2.0 and autoclave at 120° C. for 15 min |
| Solution 2 |
| 11.05 g $FeSO_4$•$7H_2O$ |
| 75 mL deionized water |
| Adjust solution to pH 1.8 with $H_2SO_4$ and filter sterilize |

Genotypic and/or Phenotypic Changes in Modified Culture Media

Genotypic Changes

Figure 4:
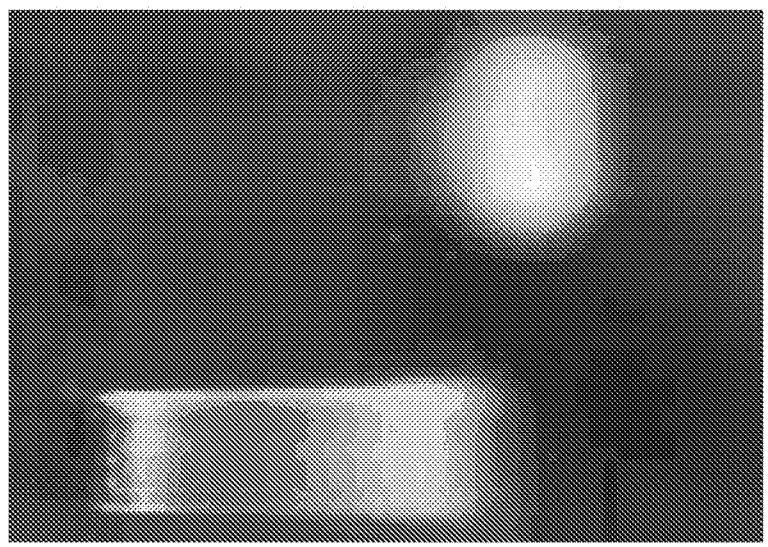
FIG. 4 demonstrates that phenotypic and genotypic changes occur when *Acidithiobacillus ferrooxidans* cells are grown in media with different proportions of organic and inorganic ingredients. Results are from a 0.8% agarose gel using DNA extracted from the *A. ferrooxidans*. Lane (L) represents a 1 kb ladder. Lane (1) shows DNA extracted from *A. ferrooxidans* grown in a medium with 75% organic content and 25% inorganic content (75/25 medium described herein) with the most prominent band at approximately 750 to 800 base pairs. Lane (2) shows DNA extracted from *A. ferrooxidans* grown in a medium with 50% organic content and 50% inorganic content (50/50 medium described herein) with the most prominent band at approximately 250 base pairs.
Figure 4:
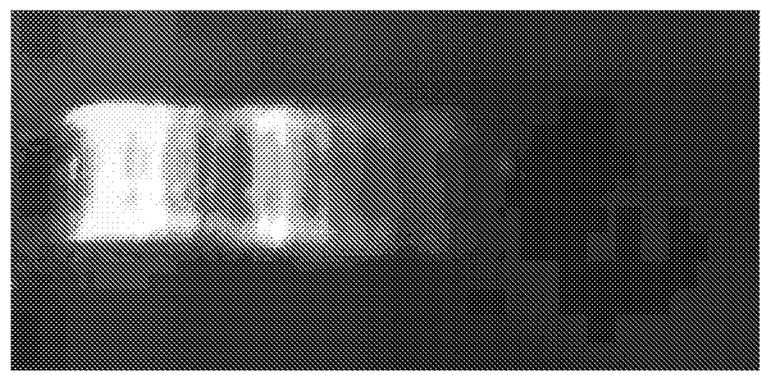

Culturing *A. ferrooxidans* in the modified culture media described herein results in changes in DNA size and expression. DNA was extracted from cultures grown in the 75/25 (Table 7) and 50/50 media (Table 3) and separated by gel electrophoresis run at 110V for 45 minutes using an 0.8% agarose gel (see FIG. 4). The primary band from the 75/25 culture was at approximately 750-800 base pairs based on comparison with a 1 kb ladder, while the primary band from the 50/50 culture was at approximately 250 base pairs.

Figure 5:
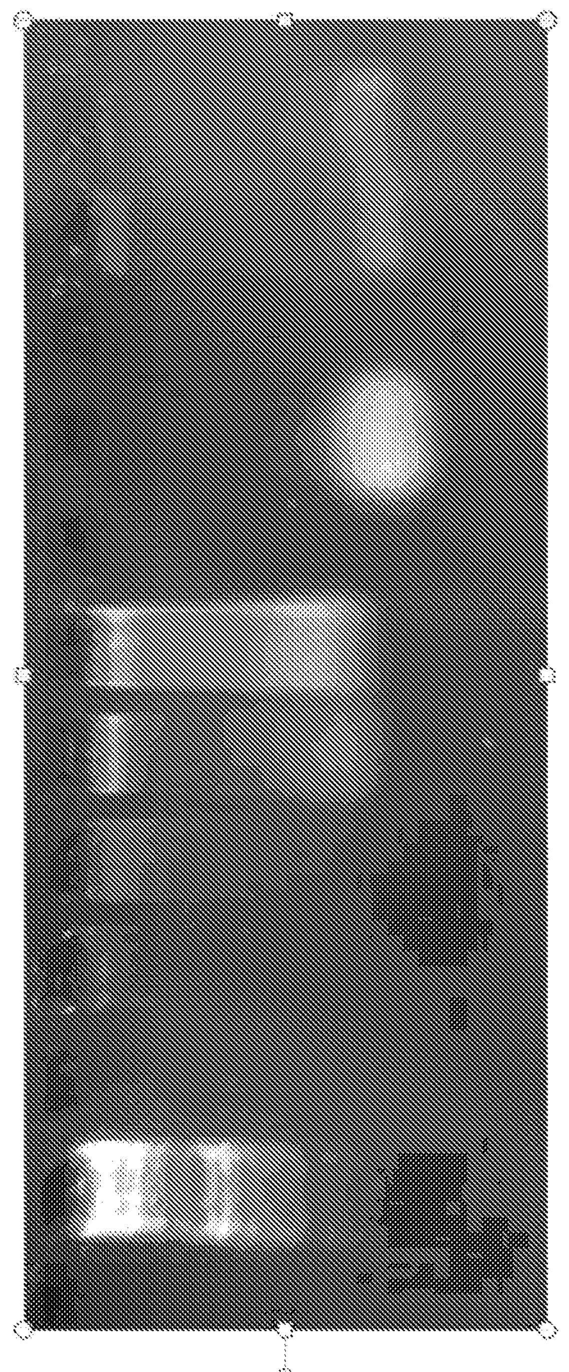
FIG. 5 shows results from 0.8% agarose gel electrophoresis analyzing DNA from *A. ferrooxidans* grown in different media and extracted using different methods. Phenotypic and/or genotypic changes are evident and not dependent on extraction method. Lane (L) is a 1 kb ladder. Lane (1) is DNA from a culture grown in 50/50 medium described herein and extracted with a commercial kit from QIAGEN. Lane (2) is DNA from a culture grown in 50/50 medium described herein and first washed with nitric acid, then extracted with a commercial kit from QIAGEN. Lane (3) is DNA from a culture grown in 75/25 medium described herein and extracted with a commercial kit from QIAGEN. Lane (4) is DNA from a culture grown in 75/25 medium described herein and first washed with nitric acid, then extracted with a commercial kit from QIAGEN. Lane (5) is DNA from a culture grown in 50/50 medium described herein and extracted using a phenol/chloroform protocol. Lane (6) is DNA from a culture grown in 75/25 medium described herein and extracted using a phenol/chloroform protocol. Lane (7) is DNA from a culture grown in 75/25 medium described herein and first washed with nitric acid, then extracted using a phenol/chloroform protocol.

To eliminate the possibility that the differences in band size related to extraction method, several different washing and extraction schemes were compared in the same 0.8% agarose gel, again run at 110V for 45 minutes. DNA from a 75/25 culture was extracted using a commercial kit from QIAGEN, a nitric acid wash followed by extraction with the QIAGEN kit, a standard phenol/chloroform protocol, or an established phenol/chloroform protocol preceded by a nitric acid wash. DNA from a 50/50 culture was extracted using a commercial kit from QIAGEN, a nitric acid wash followed by extraction with the QIAGEN kit, or an established phenol/chloroform protocol. Results are presented in FIG. 5 and indicate that different bands are a result of changes in DNA size and expression rather than extraction method.

Phenotypic Changes

Phenotypic changes were also observed in *A. ferrooxidans* cultures grown in different modified media as provided in Tables 2-7. Colonies were colored from various shades of brown to a black color, indicating different levels of oxidation and reduction of iron corresponding to different proportions of organic and inorganic components in the modified media. These phenotypic changes roughly correlate to the ability of extracts from the various cultures to provide power to an LED light in a microbial circuit or battery (see below and Table 10).

Figure 2:
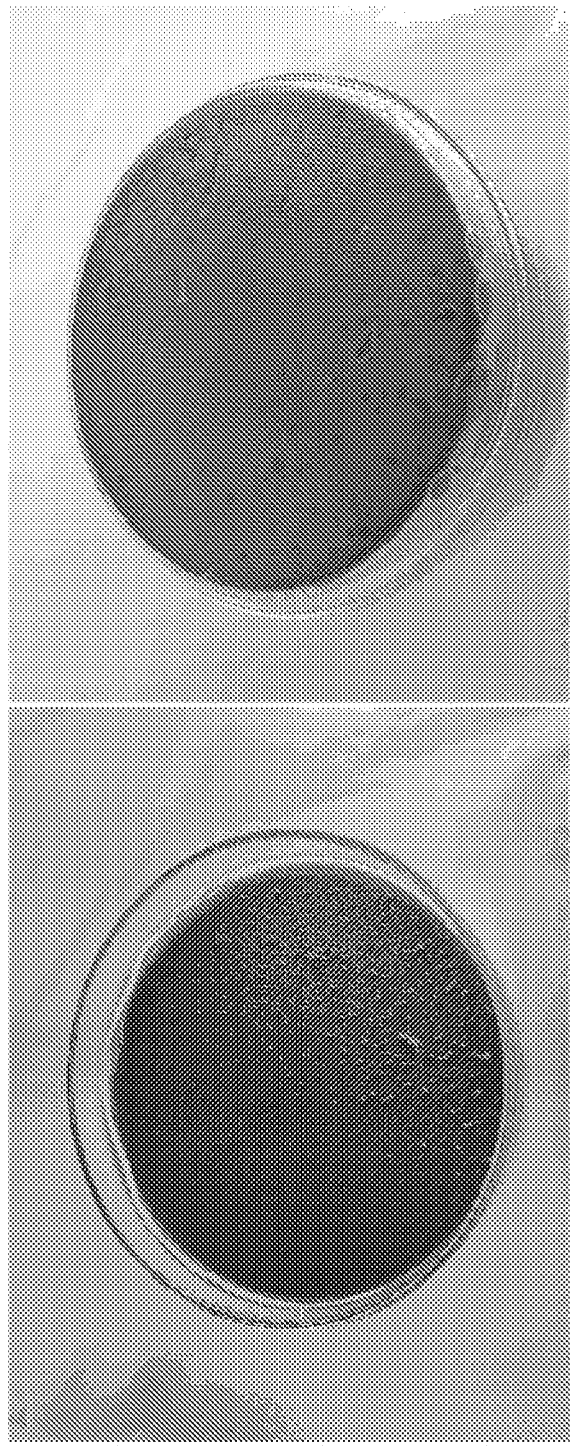
FIG. 2 shows *Acidithiobacillus ferrooxidans* grown in a culture medium consisting of 75% organic content and 25% inorganic content (75/25 medium described herein). Colonies are 100% brown.
Figure 3:
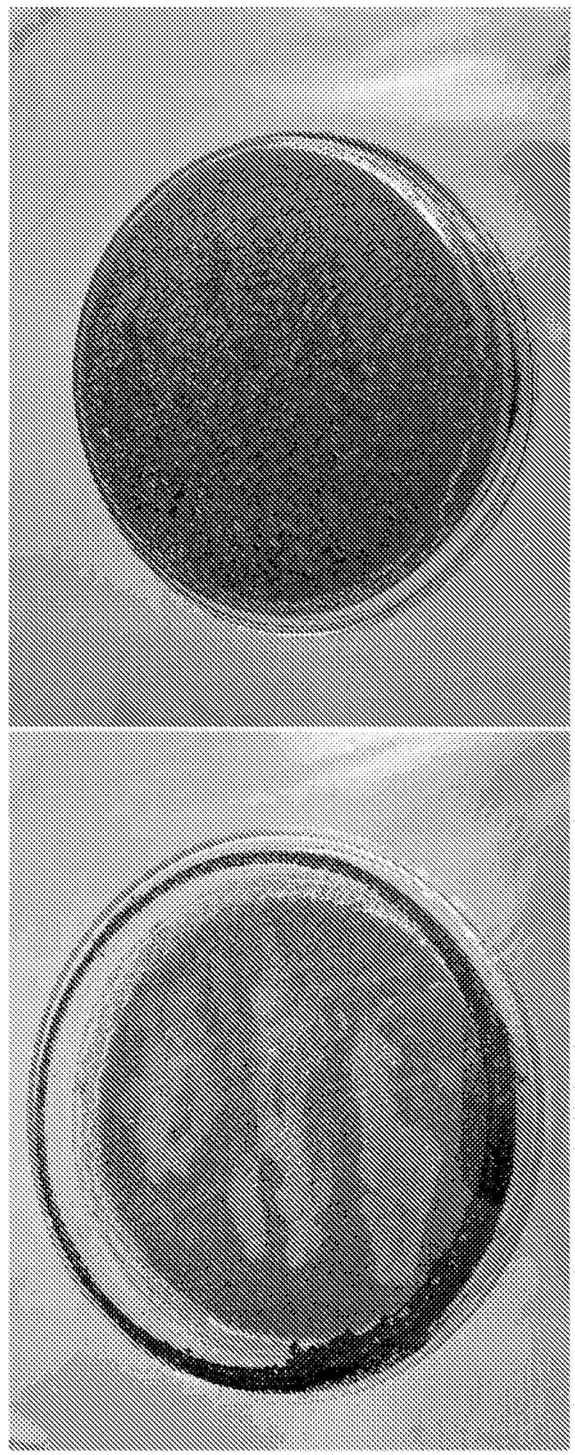
FIG. 3 shows *Acidithiobacillus ferrooxidans* grown in a culture medium consisting of 7% organic content and 93% inorganic content (7/93 medium described herein). Colonies are 90% brown.

A 50/50 medium showed approximately half of colonies as black and half as brown (see FIG. 1). A 75/25 medium showed all colonies as a brown color (see FIG. 2). A 7/93 medium showed approximately 90% of colonies as a brown color (see FIG. 3).

Production of Microbial Extracts

For the following experiments, a microbial extract was obtained from *Acidithiobacillus ferrooxidans*. Bacteria were cultured in the culture media compositions as provided in Tables 2-7 at 26° C. for 10 days. Growth (using optical density), redox potential (using an electrical redox sensor), and pH of the culture were determined during growth. Final redox potentials and pH values for each prepared extract were also determined.

After 10 days, aliquots of the *A. ferrooxidans* culture were sonicated 4 times for 2 minutes (pulses of 30 seconds with 15 second intervals between pulses) and the sonicated cultures were filtered through 0.45 μm filters. Extracts thus produced were used for further experiments or were lyophilized for storage and later reconstitution.

Determination of Biological Iron

Microbial extracts were prepared as described herein and electro conductivity (voltammetric measurement) was used to determine biological iron in the extracts. A Metrohm Voltamperimeter was used to collect measurements and 797 VA Computrance version 1.3.2 software was used to analyze data. Total iron was determined using iron (II) sulfate heptahydrate ($FeSO_4.7H_2O$, SIGMA-ALDRICH, 99% purity) as a standard.

Samples were prepared with 100 μL of extract plus 10 mL of deionized water, 100 μL of 1M catechol, and 1 mL of buffer ($Na_2HPO_4/KH_2PO_4$, pH 6.88, MERCK). Standard instrument parameters were used for experiment and are presented in Table 8:

TABLE 8

Instrument Settings for Iron Determination

| Setting | Value |
|---|---|
| Working electrode | HMDE |
| Stirrer speed | 2000 rpm |
| Mode | DP |
| Drop size | 4 |
| Calibration | Standard addition |
| Purge time | 300 s |
| Deposition potential | 0 V |
| Deposition time | 0 s |
| Equilibration time | 5 s |
| Pulse amplitude | 0.05 V |
| Start potential (condition cycles) | −0.1 V |
| End potential | −1.8 V |
| Start potential (sweep) | 0.01 V |
| End potential | −0.6 V |
| Voltage step | 0.012 V |
| Voltage step time | 0.4 s |
| Sweep rate | 0.0301 V/s |
| Peak potential Fe | −0.38 V |

Iron (II) concentration was determined by voltammetry for both cultures of *A. ferrooxidans* and extracts from cultures produced as described previously. Results are presented in Table 9:

TABLE 9

Iron (II) Concentration in *A. ferrooxidans* Cultures and Extracts[a]

| Medium | | Iron (II) Concentration (g/L) | Redox (mV) Initial | Redox (mV) Final | pH Initial | pH Final | Culture OD 550 nm | Culture OD 600 nm |
|---|---|---|---|---|---|---|---|---|
| 7/93 | Culture | 0.892 | 395 | | 2.08 | | 0.847 | 0.765 |
| | Extract | 0.895 | 403.8 | 192.6 | 2.07 | 4.05 | | |
| 50/50 | Culture | 0.659 | 448.3 | | 2.42 | | 0.774 | 0.43 |
| | Extract | 1.324 | 452.5 | 146.5 | 2.37 | 3.6 | | |
| 75/25 | Culture | 1.019 | 376.8 | | 2.94 | | 2.475 | 2.408 |
| | Extract | 1.479 | 391.1 | 297.7 | 2.78 | 4.87 | | |

[a]Measurements were taken after 10-12 days.

Construction of a Microbial Battery

Figure 6:
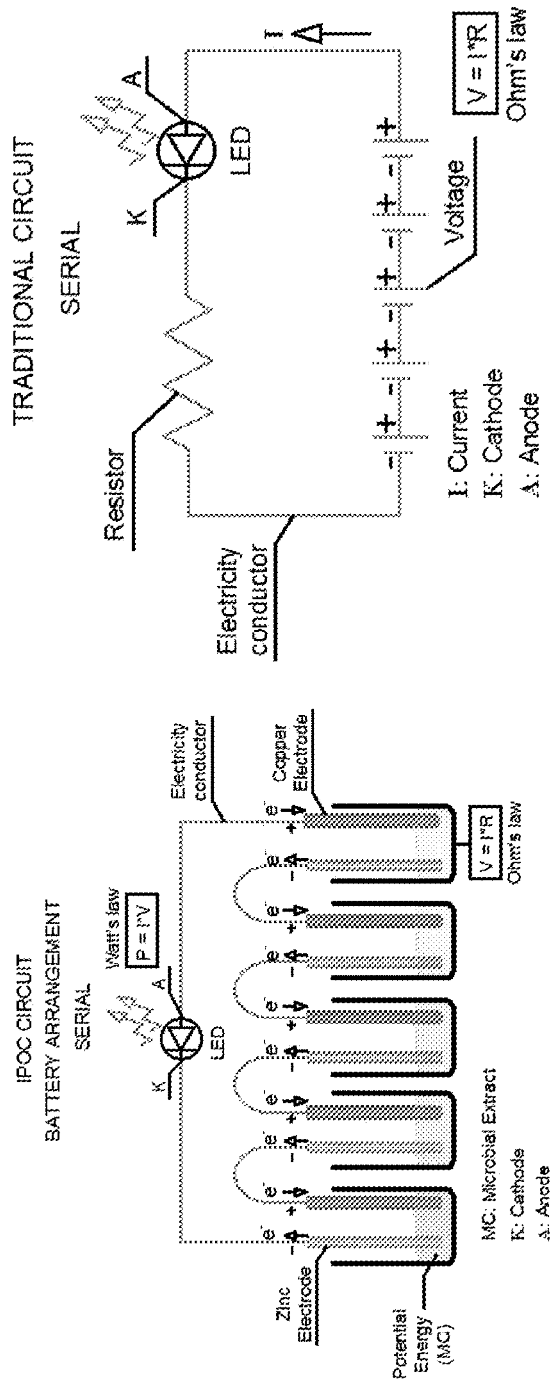
FIG. 6 shows a circuit constructed with the microbial extracts described herein plus zinc and copper electrodes described herein (left) and a standard circuit (right).
Figure 7:
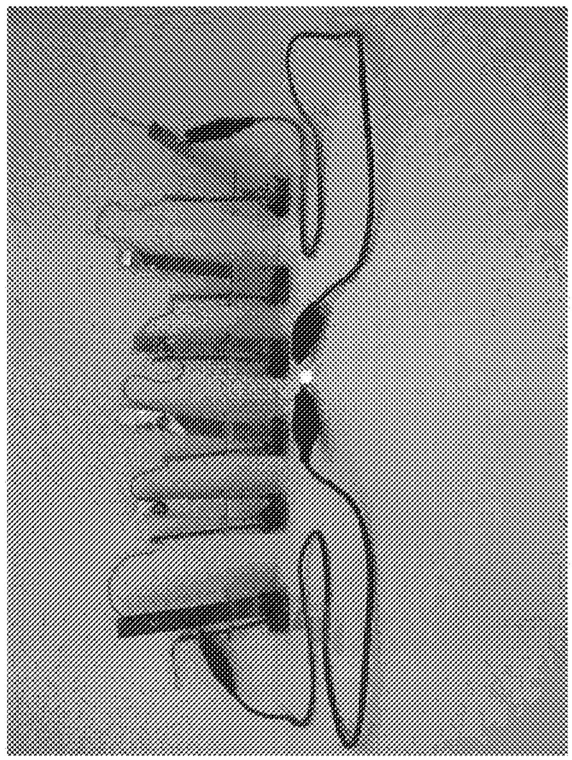
FIG. 7 shows LED light production from the circuit constructed with the microbial extracts disclosed herein (both panels).

A microbial electrical circuit was constructed as follows (FIGS. 6-7). A series of tubes was arranged in either a linear or a parallel manner. Tubes with volume capacities of 10, 15, 20, and 50 mL were evaluated, but the 50 mL capacity tubes were preferred.

25 mL aliquots of bacterial extract grown in the various media compositions described previously were placed in each tube. Five tubes were used for each experiment, but a higher number of tubes was workable if higher voltage was needed for the circuit.

Alternatively, a slurry of lyophilized extract and liquid extract was used. In a typical experiment, 1.5 g of lyophilized material and 150 μL of liquid extract were combined. Other mixtures were evaluated (1 g lyophilized extract and 50 μL of liquid extract, 1 g lyophilized extract and 200 μL of liquid extract, 2 g lyophilized extract and 200 μL of liquid extract) but were not preferred.

Following distribution of extract in the tubes, zinc and copper electrodes were introduced into each tube. Electrodes were connected to one another with appropriate wires and the circuit was closed using various colors of LED lights (e.g., white, blue, green, yellow, and red) at different luminescences or intensities. See FIG. 6 for an example microbial circuit compared to a traditional serial circuit. See also FIG. 7 wherein the microbial circuit is used to power an LED.

Effectiveness of different microbial extract circuits was assessed using commercial instruments. Voltage (V) and current (A) as well as intensity and luminescence (lux) were measured for the circuit and for light produced by the LEDs using a multimeter (MASTECH MAS830DB), a photometer (PROSKIT MT4617LD), and direct observation, as appropriate. Oxidation and reduction were measured with an electrode sensor (HATCH HQ11d). A higher current was generated the first day of experiments compared to other days. Results are presented in Table 10.

TABLE 10

Voltage, Current, Power, and LED Intensity for Microbial Circuits

| LED Color | Time | Extract Voltage (V) | | | LED Voltage (V) | | | LED Current (μA) | | | LED Power (μW) | | | LED Intensity (LUX) | | |
|---|---|---|---|---|---|---|---|---|---|---|---|---|---|---|---|---|
| λ (nm) | (day) | 7/93 | 75/25 | 50/50 | 7/93 | 75/25 | 50/50 | 7/93 | 75/25 | 50/50 | 7/93 | 75/25 | 50/50 | 7/93 | 75/25 | 50/50 |
| White | 1 | 4.6 | 4.5 | 4.6 | 2.6 | 2.5 | 2.6 | 308.0 | 51.0 | 380.0 | 803.9 | 129.0 | 972.8 | 22.0 | 21.5 | 7.4 |
| | 9 | 2.3 | 3.3 | 2.7 | 2.3 | 2.4 | 2.4 | 2.1 | 4.0 | 6.4 | 4.9 | 9.5 | 15.4 | 0.1 | 0.1 | 0.4 |
| | 14 | 3.8 | 3.2 | 4.2 | 2.5 | 2.4 | 2.5 | 14.0 | 6.2 | 20.0 | 34.7 | 15.1 | 49.6 | 1.6 | 0.7 | 3.8 |
| | 16 | 2.4 | 2.1 | 3.2 | 2.0 | 2.2 | 2.4 | 4.0 | 2.7 | 8.4 | 8.0 | 5.9 | 19.7 | 0.2 | 0.2 | 0.8 |
| | Mean[a] | 2.7 | 2.8 | 3.2 | 2.3 | 2.3 | 2.4 | 33.3 | 9.5 | 54.5 | 85.7 | 22.8 | 127.1 | 3.2 | 4.1 | 3.1 |
| | S.D.[a] | 0.8 | 0.8 | 0.8 | 0.2 | 0.2 | 0.1 | 91.2 | 14.1 | 112.2 | 238.5 | 36.1 | 286.8 | 6.5 | 7.3 | 4.5 |
| Blue (450-475) | 1 | 4.7 | 4.7 | 4.7 | 2.4 | 2.2 | 2.4 | 270.0 | 60.0 | 253.0 | 642.6 | 133.2 | 612.3 | 0.4 | 0.3 | 0.3 |
| | 9 | 2.4 | 2.6 | 2.7 | 2.3 | 2.2 | 2.4 | 3.3 | 3.3 | 7.1 | 7.6 | 7.1 | 16.7 | 0.0 | 0.0 | 0.0 |
| | 14 | 3.8 | 2.8 | 3.8 | 2.4 | 2.4 | 2.4 | 16.0 | 3.8 | 14.5 | 38.6 | 9.0 | 35.1 | 4.7 | 2.0 | 3.4 |
| | 16 | 2.3 | 2.3 | 2.6 | 2.3 | 2.0 | 2.3 | 5.0 | 5.0 | 5.8 | 11.3 | 9.8 | 13.6 | 1.8 | 0.9 | 2.0 |
| | Mean | 2.6 | 2.6 | 3.3 | 2.3 | 2.2 | 2.4 | 30.1 | 9.8 | 48.6 | 71.4 | 22.0 | 118.0 | 0.8 | 0.3 | 0.6 |
| | S.D. | 0.9 | 0.7 | 0.7 | 0.1 | 0.1 | 0.0 | 79.7 | 16.7 | 78.1 | 189.7 | 37.2 | 190.1 | 1.4 | 0.6 | 1.1 |
| Green (495-570) | 1 | 4.6 | 4.7 | 4.6 | 2.2 | 2.2 | 2.3 | 330.0 | 65.0 | 280.0 | 726.0 | 141.7 | 632.8 | 18.5 | 21.3 | 18.1 |
| | 9 | 2.4 | 3.0 | 2.6 | 2.1 | 2.1 | 2.1 | 5.8 | 5.3 | 9.3 | 11.9 | 10.9 | 19.1 | 0.5 | 0.2 | 0.1 |
| | 14 | 2.8 | 3.3 | 4.1 | 2.2 | 2.1 | 2.2 | 17.4 | 8.4 | 19.0 | 37.4 | 18.0 | 41.4 | 3.9 | 2.6 | 1.2 |
| | 16 | 2.8 | 2.0 | 1.3 | 2.0 | 1.9 | 2.1 | 8.0 | 4.4 | 130 | 15.9 | 8.4 | 27.4 | 0.5 | 0.8 | 1.9 |
| | Mean | 2.7 | 3.0 | 2.9 | 2.1 | 2.1 | 2.1 | 42.2 | 12.4 | 40.4 | 91.7 | 26.2 | 89.4 | 4.0 | 3.6 | 5.8 |
| | S.D. | 0.7 | 0.7 | 0.9 | 0.1 | 0.1 | 0.1 | 96.1 | 17.6 | 80.2 | 211.7 | 38.6 | 181.9 | 6.1 | 6.4 | 7.9 |
| Yellow (570-590) | 1 | 4.7 | 4.6 | 4.7 | 1.9 | 1.8 | 1.8 | 290.0 | 75.0 | 275.0 | 536.5 | 132.8 | 503.3 | 17.8 | 16.8 | 14.4 |
| | 9 | 2.2 | 2.5 | 1.9 | 1.7 | 1.6 | 1.6 | 8.4 | 6.5 | 8.0 | 13.9 | 10.5 | 13.1 | 0.0 | 0.1 | 0.1 |
| | 14 | 3.8 | 3.1 | 3.4 | 1.7 | 1.7 | 1.8 | 15.0 | 6.0 | 23.0 | 26.0 | 10.2 | 40.3 | 0.0 | 0.0 | 0.1 |
| | 16 | 2.5 | 2.5 | 3.2 | 1.6 | 1.7 | 1.7 | 9.4 | 10.0 | 9.5 | 15.2 | 16.6 | 15.9 | 0.0 | 0.0 | 0.0 |
| | Mean | 2.5 | 3.0 | 2.8 | 1.7 | 1.7 | 1.7 | 39.8 | 15.4 | 40.9 | 71.1 | 26.2 | 72.8 | 2.1 | 2.3 | 2.1 |
| | S.D. | 1.0 | 0.6 | 0.8 | 0.1 | 0.0 | 0.1 | 83.6 | 20.1 | 79.7 | 155.3 | 35.9 | 146.3 | 5.3 | 5.2 | 4.4 |
| Red (620-750) | 1 | 4.7 | 4.6 | 4.6 | 1.8 | 1.7 | 1.7 | 290.0 | 77.0 | 307.0 | 513.3 | 131.7 | 534.2 | 17.5 | 5.9 | 8.5 |
| | 9 | 2.4 | 2.1 | 2.5 | 1.6 | 1.6 | 1.6 | 13.0 | 7.0 | 14.7 | 20.8 | 11.0 | 23.2 | 0.2 | 0.2 | 0.1 |
| | 14 | 3.9 | 3.3 | 3.9 | 1.6 | 1.6 | 1.6 | 17.0 | 1.2 | 21.0 | 27.2 | 1.9 | 34.2 | 0.5 | 0.1 | 0.3 |
| | 16 | 2.8 | 2.8 | 2.6 | 1.6 | 1.5 | 1.6 | 10.0 | 7.0 | 11.7 | 15.8 | 10.4 | 18.4 | 0.1 | 0.0 | 0.0 |
| | Mean | 2.8 | 2.9 | 3.0 | 1.6 | 1.6 | 1.6 | 43.8 | 15.7 | 52.3 | 75.0 | 25.7 | 88.2 | 2.5 | 1.3 | 1.5 |
| | S.D. | 0.8 | 0.7 | 0.9 | 0.1 | 0.1 | 0.1 | 82.7 | 20.8 | 90.1 | 147.0 | 35.9 | 157.0 | 5.1 | 1.8 | 2.5 |

[a]Mean and standard deviation are calculated from daily measurements taken over the course of 16 days.

Carbo-Ionic Extracts as Culture Media and Culture Media Supplements

In one aspect, described herein are methods for enhancing the growth of microorganisms such as, for example, those of commercial interest. Initial experiments were conducted on *Saccharomyces cerevisiae* (strain ATCC 201396).

Yeasts were grown under the following sets of conditions: (1) control with no added iron (i.e., grown in standard yeast malt media only); (2) yeast with 15 mg/L iron added; (3) yeast grown with extract produced by *A. ferrooxidans* cultured in 7/93 medium described above; (4) yeast grown with extract produced by *A. ferrooxidans* cultured in 50/50 medium; and (5) yeast grown with extract produced by *A. ferrooxidans* cultured in 75/25 medium. Nucleic acid concentration (using optical density measurements and comprising both DNA and RNA) is used as a measure for cell growth and is presented in Table 11 below:

TABLE 11

Nucleic Acids Content of Yeast Cultures

| Sample | Nucleic Acids Concentration (ng/μL) |
|---|---|
| Control | 2385 |
| Yeast with Commercial Iron | 1647 |
| Yeast with 7 Organic/93 Inorganic Culture Extract | 21,695 |
| Yeast with 50 Organic/50 Inorganic Culture Extract | 23,915 |
| Yeast with 75 Organic/25 Inorganic Culture Extract | 240 |

The cultures grown with the largest concentrations of *A. ferrooxidans* extract exhibit the highest nucleic acids concentrations, thus demonstrating the efficacy of this extract as a media or media additive.

Yeast growth was measured by cell growth to confirm the nucleic acids results. Colony forming units (CFU) were counted for yeasts grown in the 9K, 75/25, and 50/50 extracts described herein as well as with a commercial iron supplement. Results are presented in Table 12 below:

TABLE 12

CFU for *S. cerevisiae* Grown in Different Iron-Containing Media

| Medium | Initial CFU | CFU After 24 Hours | CFU After 48 Hours | CFU After 72 Hours |
|---|---|---|---|---|
| 9K | 0 | $1.04 \times 10^8$ | $2.11 \times 10^8$ | $2.33 \times 10^8$ |
| 75/25 | 0 | $1.63 \times 10^8$ | $2.34 \times 10^8$ | $2.45 \times 10^8$ |
| 50/50 | 0 | $1.60 \times 10^8$ | $1.81 \times 10^8$ | $1.38 \times 10^8$ |
| Commercial Iron | 0 | $0.12 \times 10^8$ | $0.43 \times 10^8$ | $3.33 \times 10^8$ |

Figure 8:
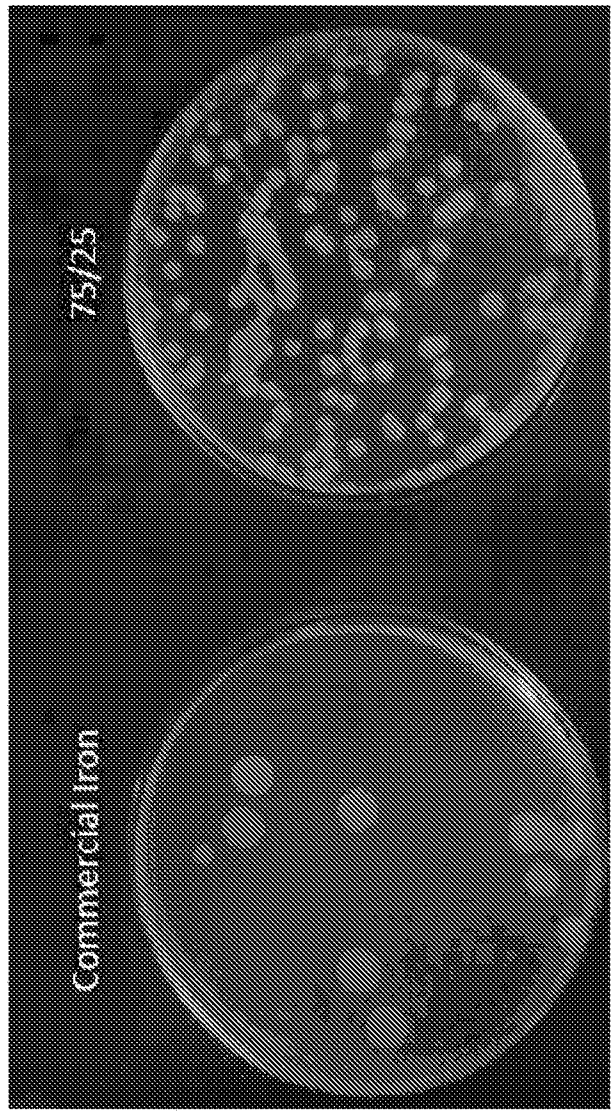
FIG. 8 shows *Saccharomyces cerevisiae* cultures grown with a commercial iron medium (left) and an extract produced by growing *A. ferrooxidans* in a 75/25 medium as described herein. Colony forming units (CFU) are higher in the *S. cerevisiae* grown in the extract disclosed herein.

After 48 hours, CFU counts were higher for all modified media as compared to commercial iron, thus confirming the nucleic acids results. Plates with yeast colonies grown with a commercial iron supplement and the modified 75/25 media described herein are shown in FIG. 8.

Similar experiments were performed in liquid cultures and microorganism growth and reproduction was assessed using optical density. Aliquots were removed from the liquid cultures at 0, 24, 48, and 72 hours. Results are presented below in Table 13.

TABLE 13

| Optical Density for *S. cerevisiae* Grown in Different Iron-Containing Media | | | | |
|---|---|---|---|---|
| Medium | Initial Culture | OD After 24 Hours | OD After 48 Hours | OD After 72 Hours |
| 9K | 0.015 | 2.001 | 2.127 | 2.170 |
| 75/25 | 0.025 | 1.944 | 2.062 | 2.124 |
| 50/50 | 0.020 | 1.951 | 2.063 | 2.112 |
| Commercial Iron | 0.027 | 1.399 | 2.052 | 2.211 |

Methods for Enhancing the Growth of Plants

Effects of the extracts and compositions disclosed herein on plant growth and development were tested on tomato tissue culture samples. Tomato calluses were grown for five weeks in standard M&S medium with 27.8 mg/L of *A. ferrooxidans* culture extract produced as described above. Extracts of *A. ferrooxidans* cultured in 50/50 and 75/25 media as described above were tested alongside a control to which a commercial iron product had been added. Results are presented in Table 14.

TABLE 14

| Morphological Characteristics of Plants and Plant Calluses Treated with *A. ferrooxidans* Culture Extracts | | | | | |
|---|---|---|---|---|---|
| Time (weeks) | 0 | 1 | 3 | 4 | 5 |
| 50/50 Media | | | | | |
| Plant Height (cm) | 0.884 | 1.284 | 2.976 | 3.122 | 3.553 |
| Number of Leaves | 1 | 3 | 5 | 6 | 6 |
| % Roots | 28 | 52 | 80 | 87 | 90 |
| Leaf Area ($cm^2$) | N/A | N/A | 1.5 | 1.6 | 1.6 |
| 75/25 Media | | | | | |
| Plant Height (cm) | 0.352 | 1.06 | 2.024 | 2.493 | 2.984 |
| Number of Leaves | 1 | 2 | 5 | 6 | 6 |
| % Roots | 32 | 40 | 64 | 70 | 70 |
| Leaf Area ($cm^2$) | N/A | N/A | 0.75 | 0.94 | 1.02 |
| Control | | | | | |
| Plant Height (cm) | 0.8916 | 1.332 | 1.816 | 2.006 | 2.345 |
| Number of Leaves | 2 | 3 | 5 | 6 | 7 |
| % Roots | 12 | 20 | 52 | 60 | 65 |
| Leaf Area ($cm^2$) | N/A | N/A | 0.67 | 0.79 | 0.79 |

The samples treated with either modified 50/50 or 75/25 media had taller average heights, greater percentages of roots, and greater leaf area than the control, showing the efficacy of treating tissue culture samples with *A. ferrooxidans* extract to promote plant growth and development.

Effect of Culture and/or Extract of the *Acidithiobacillus ferrooxidans* in Growth of the Tomato Tissue Culture (Callus)

Tomato tissue culture (callus) grown for five (5) weeks in standard medium Murashige and Skoog (M&S) following standard protocol (Murashige, T; Skoog, F (1962). "A Revised Medium for Rapid. Growth and Bio Assays with Tobacco Tissue Cultures". *Physiologia Plantarum.* 15 (3): 473-497. 50/50: Organic (50%)—Inorganic (50%) (and commercial Iron was used as the control with the same concentration of 27.8 mg/L).

All calluses were grown inside same size and volume flasks (250 ml) and covered with aluminum foil and girish paper (plastic paper) following the standard protocol (see photo). Calluses initial size were 0.7 cm without leaves and roots, and their weight was 0.6 g.

Results were obtained after 3, 4, 6, 7, 8, 11, and 13 weeks when the roots and leaves were clearly showing. Morphological parameters (i.e. height, number of leaves, root percentage, and leaf area) for Tomato tissue culture (callus) grown with 50/50. 75/25 extracts of the *Acidithiobacillus ferrooxidans* and Commercial Iron extract.

Table 15 shows morphological parameters for Tomato tissue culture (callus) grown with 50/50 extracts from the *A. ferrooxidans* culture. Results of Height, number of leaves and leaf area are shown in mean. % Root was calculated using the following formula: % Root=(Vroot*100%)/Vagar (Vroot=volume of the geometric figure of the roots; Vagar=Volume that the medium takes in the flask. Table 16 shows morphological parameters for Tomato tissue culture (callus) grown with Commercial iron solutions.

TABLE 15

| Extract 50/50: Organic (50%) - Inorganic (50%) | | | | | | | |
|---|---|---|---|---|---|---|---|
| Weeks | 3 | 4 | 6 | 7 | 8 | 11 | 13 |
| Height (cm) | 0.884 | 1.284 | 2.976 | 3.122 | 3.553 | 3.565 | 3.632 |
| N. Leaves | 1 | 3 | 5 | 6 | 6 | 7 | 9 |
| % Root | 28% | 52% | 80% | 87% | 90% | 95% | 97% |
| Leaf area ($cm^2$) | NA | NA | 1.5 | 1.6 | 1.6 | 1.7 | 1.7 |

TABLE 16

| Commercial Iron | | | | | | | |
|---|---|---|---|---|---|---|---|
| | 3 week | 4 week | 6 week | 7 week | 8 week | 11 week | 13 week |
| Height (cm) | 0.8916 | 1.332 | 1.816 | 2.006 | 2.345 | 2.573 | 2.741 |
| N. Leaves | 2 | 3 | 5 | 6 | 7 | 7 | 9 |
| % Root | 12% | 20% | 52% | 60% | 65% | 65% | 66% |
| Leaf area ($cm^2$) | NA | NA | 0.67 | 0.79 | 0.79 | 0.82 | 0.87 |

Throughout this application, various publications are referenced. The disclosures of these publications in their entireties are hereby incorporated by reference into this application in order to more fully describe the compounds, compositions, and methods described herein.

Various modifications and variations can be made to the compounds, compositions, and methods described herein. Other aspects of the compounds, compositions, and methods described herein will be apparent from consideration of the specification and practice of the compounds, compositions, and methods disclosed herein. It is intended that the specification and examples be considered as exemplary.

What is claimed:

1. A method for producing an extract comprising culturing a microorganism that produces iron (II) ions in a culture medium comprising an organic component and an inorganic component; wherein the microorganism consists of *Acidithiobacillus ferroxidans*; and wherein the organic component comprises a meat extract, a yeast extract, and a peptone.

2. The method of claim 1, wherein the organic component further comprises a salt.

3. The method of claim 2, wherein the salt is sodium chloride.

4. The method of claim 1, wherein the meat extract is present in an amount of from 0.1 g/L to 5 g/L.

5. The method of claim 1, wherein the yeast extract is present in an amount of from 0.1 g/L to 5 g/L.

6. The method of claim 1, wherein the peptone is present in an amount of from 0.1 g/L to 10 g/L.

7. The method of claim 2, wherein the salt is present in an amount of from 0.1 g/L to 10 g/L.

8. The method of claim 2, wherein the organic component comprises water, a meat extract in the amount of from 0.1 to 5 g/L, a yeast extract in the amount of 0.1 to 5 g/L, a peptone in the amount of from 0.1 to 10 g/L, and a salt in the amount of from 0.1 to 10 g/L.

9. The method of claim 1, wherein the inorganic component comprises an iron salt.

10. The method of claim 9, wherein the inorganic component comprises iron (II) ions at a concentration of from 50 to 200 mM.

11. The method of claim 9, wherein the inorganic component further comprises a potassium salt, an ammonium salt, a magnesium salt, a calcium salt, or any combination thereof.

12. The method of claim 11, wherein the inorganic comprises potassium ions at a concentration of from 1 to 25 mM.

13. The method of claim 11, wherein the inorganic component comprises ammonium ions at a concentration of from 5 to 75 mM.

14. The method of claim 11, wherein the inorganic component comprises magnesium ions at a concentration of from 1 to 10 mM.

15. The method of claim 11, wherein the inorganic component comprises calcium ions at a concentration of from 10 to 100 μm.

16. The method of claim 11, wherein the inorganic component comprises potassium ions at a concentration of from 1 to 25 mM, ammonium ions at a concentration of from 5 to 75 mM, magnesium ions at a concentration of from 1 to 10 mM, and calcium ions at a concentration of from 10 to 100 μm.

17. The method of claim 9, wherein the inorganic component has a pH of less than or equal to 3.

18. The method of claim 9, wherein the inorganic component has a pH of less than or equal to 2.

19. The method of claim 1, wherein the culture medium comprises:

(a) an organic component comprising water, a meat extract in the amount of from 0.1 to 5 g/L, a yeast extract in the amount of 0.1 to 5 g/L, a peptone in the amount of from 0.1 to 10 g/L, and a salt in the amount of from 0.1 to 10 g/L; and (b) an inorganic component comprising water, potassium ions at a concentration of from 1 to 25 mM, ammonium ions at a concentration of from 5 to 75 mM, magnesium ions at a concentration of from 1 to 10 mM, and calcium ions at a concentration of from 10 to 100 μm, wherein the volume ratio of organic component to inorganic component is from 5:1 to 1:5.

20. The method of claim 19, wherein the volume ratio of organic component to inorganic component is from 2:1 to 1:2.

21. The method of claim 19, wherein the volume ratio of organic component to inorganic component is from 1.5:1 to 1:1.5.

22. The method of claim 1, wherein the extract is formulated as a liquid, a slurry, a powder, or a mixture thereof.

* * * * *